US012792847B2

(12) United States Patent
Dhodapkar et al.

(10) Patent No.: US 12,792,847 B2
(45) Date of Patent: Nov. 10, 2026

(54) ARTIFICIAL INTELLIGENCE SYSTEMS AND METHODS FOR ENABLING NATURAL LANGUAGE TRANSCRIPTOMICS ANALYSIS

(71) Applicant: Yale University, New Haven, CT (US)

(72) Inventors: Rahul Dhodapkar, Los Angeles, CA (US); David van Dijk, New Haven, CT (US)

(73) Assignee: YALE UNIVERSITY, New Haven, CT (US)

( * ) Notice: Subject to any disclaimer, the term of this patent is extended or adjusted under 35 U.S.C. 154(b) by 151 days.

(21) Appl. No.: 18/928,680

(22) Filed: Oct. 28, 2024

(65) Prior Publication Data

US 2025/0139386 A1 May 1, 2025

Related U.S. Application Data

(60) Provisional application No. 63/593,753, filed on Oct. 27, 2023.

(51) Int. Cl.
*G06F 40/40* (2020.01)
*G06N 3/0475* (2023.01)
(Continued)

(52) U.S. Cl.
CPC .......... *G06F 40/40* (2020.01); *G06N 3/0475* (2023.01); *G06N 3/096* (2023.01); *G16B 25/10* (2019.02); *G16B 30/00* (2019.02); *G16B 40/20* (2019.02)

(58) Field of Classification Search
CPC .......... G06F 40/40; G16B 25/10; G16B 40/20
See application file for complete search history.

(56) References Cited

U.S. PATENT DOCUMENTS 10,540,591 B2 1/2020 Gao et al.
11,482,305 B2 10/2022 Barbour et al.
(Continued)

OTHER PUBLICATIONS

Miller, D., Stern, A., & Burstein, D. (2022). Deciphering microbial gene function using natural language processing. Nature Communications, 13(1), 5731. (Year: 2022).*
(Continued)

*Primary Examiner* — Ibrahim Siddo
(74) *Attorney, Agent, or Firm* — Troutman Pepper Locke LLP

(57) ABSTRACT

The disclosed technology relates to methods, transcriptomics systems, and non-transitory computer readable media for enabling natural language transcriptomics analysis. In some examples, genomic data including gene expression profiles for cells is transformed into sequences of genes ordered by expression level for each of the cells. The sequences of genes are annotated with metadata in a natural language format. A large language model (LLM) is then fine-tuned using the annotated sequences. The LLM is pretrained for natural language processing (NLP) tasks. The fine-tuned LLM is applied to generate and output a result in response to a received prompt in the natural language format. Thus, the LLMs of this technology advantageously both generate and interpret transcriptomics data and interact in natural language to generate meaningful text from cells and valid genes, among many other types of results.

20 Claims, 17 Drawing Sheets
(10 of 17 Drawing Sheet(s) Filed in Color)

(51) Int. Cl.

| | |
|---|---|
| ***G06N 3/096*** | (2023.01) |
| ***G16B 25/10*** | (2019.01) |
| ***G16B 30/00*** | (2019.01) |
| ***G16B 40/20*** | (2019.01) |

(56) References Cited

U.S. PATENT DOCUMENTS

| | | | | |
|---|---|---|---|---|
| 11,705,219 | B2 | 7/2023 | Schulz-Trieglaff et al. | |
| 2018/0102190 | A1 | 4/2018 | Hogue et al. | |
| 2023/0144683 | A1 * | 5/2023 | Chatterjee .............. | G06N 3/088 435/7.21 |

OTHER PUBLICATIONS

Cui et al., scGPT: Towards Building a Foundation for Single-Cell Multi-omics Using Generative AI, bioRxiv the Preprint Server for Biology, Jul. 2, 2023, https://www.biorxiv.org/content/10.1101/2023.04.30.538439v2.

Theodoris et al., Transfer learning enables predictions in network biology, Nature vol. 618, Jun. 15, 2023, pp. 616-624, https://www.nature.com/articles/s41586-023-06139-9.

Lee et al., Immunophenotyping of COVID-19 and influenza highlights the role of type I interferons in development of severe COVID-19, Science Immunology 5, Jul. 10, 2020, pp. 1-13.

Dhodapkar, Representing cells as sentences enables natural-language processing for single-cell transcriptomics, bioRxiv the Preprint Server for Biology, Sep. 19, 2022, pp. 1-8, https://www.biorxiv.org/content/10.1101/2022.09.18.508438v1.

Hao et al., Large Scale Foundation Model on Single-cell Transcriptomics, bioRxiv the Preprint Server for Biology, Jun. 2, 2023, https://doi.org/10.1101/2023.05.29.542705.

* cited by examiner

| Model | Gen. Length | Valid Genes % | Unique Genes % |
|---|---|---|---|
| GPT-2 Small (C2S) | 101.54 | 97.84 | 97.31 |
| GPT-2 Small (NL + C2S) | 99.84 | 99.60 | 98.88 |
| GPT-2 Medium (C2S) | 100.62 | 97.51 | 96.69 |
| GPT-2 Medium (NL + C2S) | 99.80 | 99.70 | 99.47 |

FIG. 8

| Model | Accuracy | F1 | Precision | Recall |
|---|---|---|---|---|
| Random Classifier | 2.86 | 2.69 | 2.86 | 2.57 |
| GPT-2 Small (C2S) | 29.33 | 17.46 | 13.27 | 29.33 |
| GPT-2 Small (NL + C2S) | 69.95 | 68.56 | 69.44 | 69.95 |
| GPT-2 Medium (C2S) | 29.17 | 17.41 | 13.35 | 19.17 |
| GPT-2 Medium (NL + C2S) | 74.26 | 73.69 | 74.16 | 74.26 |

FIG. 9

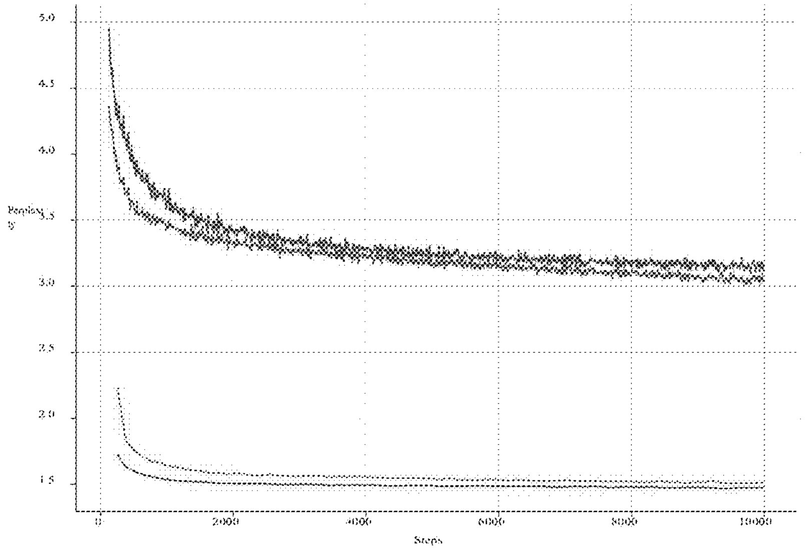
FIG. 10A
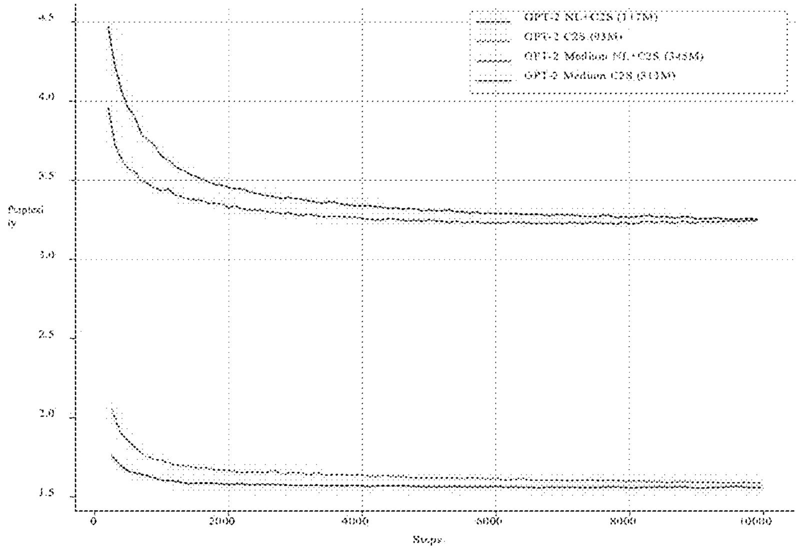
FIG. 10B
| Model | Pearson R | Spearman R | $R_2$ |
|---|---|---|---|
| GPT-2 Small (C2S) | 0.947 | 0.766 | 0.873 |
| GPT-2 Small (NL + C2S) | 0.984 | 0.768 | 0.949 |
| GPT-2 Medium (C2S) | 0.948 | 0.781 | 0.88 |
| GPT-2 Medium (NL + C2S) | 0.982 | 0.781 | 0.943 |
FIG. 11

| Model | K=5 Expr. | Lev. | K=10 Expr. | Lev. | K=25 Expr. | Lev. | K=50 Expr. | Lev. |
|---|---|---|---|---|---|---|---|---|
| Real cells (ground truth): | 62.60 | 37.55 | 62.32 | 39.86 | 60.45 | 42.64 | 58.31 | 44.33 |
| Generated cells: | | | | | | | | |
| scVI | 43.06 | - | 44.24 | - | 45.06 | - | 43.63 | - |
| GPT-2 Small (C2S) | 24.56 | 16.02 | 23.79 | 17.72 | 23.51 | 19.17 | 22.84 | 19.76 |
| GPT-2 Small (NL + C2S) | 52.55 | 37.63 | 52.19 | 41.20 | 51.42 | 43.42 | 49.51 | 44.44 |
| GPT-2 Medium (C2S) | 26.36 | 17.58 | 25.48 | 19.18 | 24.55 | 20.67 | 23.44 | 21.32 |
| GPT-2 Medium (NL + C2S) | 54.67 | 38.60 | 54.52 | 41.34 | 53.27 | 43.93 | 51.80 | 44.73 |

FIG. 13

| Model | K=5 Expr. | Lev. | K=10 Expr. | Lev. | K=25 Expr. | Lev. | K=50 Expr. | Lev. |
|---|---|---|---|---|---|---|---|---|
| scVI | 45.72 | - | 47.04 | - | 45.36 | - | 39.90 | - |
| GPT-2 Small (C2S) | 28.65 | 70.61 | 30.03 | 52.26 | 31.68 | 40.88 | 32.66 | 36.21 |
| GPT-2 Small (NL + C2S) | 60.07 | 76.09 | 60.41 | 66.95 | 60.55 | 60.04 | 59.42 | 56.80 |
| GPT-2 Medium (C2S) | 32.28 | 69.57 | 34.00 | 54.50 | 34.57 | 43.93 | 33.78 | 39.71 |
| GPT-2 Medium (NL + C2S) | 62.95 | 76.67 | 62.98 | 67.77 | 63.09 | 60.95 | 62.05 | 57.51 |

FIG. 14

| Model | k-NN (↑) 3 | 5 | 10 | 25 | GW (↓) |
|---|---|---|---|---|---|
| scGen | 0.2376 ± 0.0112 | 0.2330 ± 0.0093 | 0.2377 ± 0.0053 | 0.2335 ± 0.0041 | 315.9505 ± 1.2431 |
| scVI | 0.2436 ± 0.0062 | 0.2400 ± 0.0064 | 0.2425 ± 0.0034 | 0.2348 ± 0.0032 | 302.1285 ± 0.9338 |
| scDiffusion | 0.2335 ± 0.0125 | 0.2288 ± 0.0111 | 0.2368 ± 0.0067 | 0.2306 ± 0.0049 | 72.0208 ± 0.3937 |
| scGPT | 0.1838 ± 0.0086 | 0.1788 ± 0.0169 | 0.1811 ± 0.0149 | 0.1882 ± 0.0071 | 2989.8066 ± 4.9229 |
| C2S (Pythia-160m) | **0.2588 ± 0.0061** | **0.2565 ± 0.0060** | **0.2746 ± 0.0073** | **0.2715 ± 0.0070** | **54.3040 ± 0.3410** |

FIG. 15

| Prompts | k-NN (↑) 3 | 5 | 10 | 25 |
|---|---|---|---|---|
| Seen | 0.2588 ± 0.0061 | 0.2565 ± 0.0060 | 0.2746 ± 0.0073 | 0.2715 ± 0.0070 |
| Unseen | 0.1983 ± 0.0050 | 0.1949 ± 0.0067 | 0.2083 ± 0.0065 | 0.2022 ± 0.0056 |

FIG. 16

| | Model | Pearson R | Top-20 DE Pearson R | Spearman R | Top-20 DE Spearman R |
|---|---|---|---|---|---|
| | scGen | 0.6805 ± 0.0075 | 0.7187 ± 0.0054 | 0.5654 ± 0.0025 | 0.6256 ± 0.0074 |
| | scGPT | 0.0041 ± 0.0018 | 0.1299 ± 0.0495 | -0.0002 ± 0.0040 | 0.1440 ± 0.0996 |
| | C2S (Pythia-160m) | **0.9241 ± 0.0002** | **0.9734 ± 0.0007** | **0.6210 ± 0.0005** | **0.9752 ± 0.0016** |
| Δ | scGen | 0.3871 ± 0.0060 | **0.3743 ± 0.0167** | 0.2586 ± 0.0030 | 0.3999 ± 0.0103 |
| Δ | scGPT | 0.0980 ± 0.0001 | 0.0213 ± 0.0001 | 0.0689 ± 0.0019 | 0.0441 ± 0.0006 |
| Δ | C2S (Pythia-160m) | **0.4829 ± 0.0008** | **0.3789 ± 0.0042** | **0.2895 ± 0.0009** | **0.4528 ± 0.0092** |

FIG. 17

| | Model | Cytokine Stimulation | | L1000 | | GTEx | |
|---|---|---|---|---|---|---|---|
| | | Acc | AUROC | Acc | AUROC | Acc | AUROC |
| Partial label | k-NN Classifier | 0.462 ± 0.0047 | 0.550 ± 0.0064 | 0.592 ± 0.0054 | 0.740 ± 0.0036 | 0.492 ± 0.0047 | 0.662 ± 0.0035 |
| | XGBoost | 0.515 ± 0.0175 | 0.631 ± 0.0202 | 0.389 ± 0.0066 | 0.534 ± 0.0044 | 0.482 ± 0.0127 | 0.633 ± 0.0120 |
| | Geneformer | 0.600 ± 0.0170 | 0.722 ± 0.0145 | 0.419 ± 0.0153 | 0.632 ± 0.0181 | 0.500 ± 0.0013 | 0.649 ± 0.0025 |
| | scGPT | 0.419 ± 0.0001 | 0.500 ± 0.0000 | 0.334 ± 0.0076 | 0.500 ± 0.0000 | 0.270 ± 0.0522 | 0.500 ± 0.0000 |
| | C2S (GPT-2 Large) | **0.639 ± 0.0049** | **0.767 ± 0.0049** | **0.631 ± 0.0031** | **0.768 ± 0.0021** | **0.575 ± 0.0035** | **0.713 ± 0.0014** |
| Full label | k-NN Classifier | 0.060 ± 0.0044 | 0.509 ± 0.0013 | 0.168 ± 0.0041 | 0.583 ± 0.0020 | 0.112 ± 0.0027 | 0.500 ± 0.0001 |
| | XGBoost | 0.087 ± 0.0088 | 0.528 ± 0.0050 | 0.124 ± 0.0032 | 0.556 ± 0.0018 | 0.107 ± 0.0080 | 0.500 ± 0.0003 |
| | Geneformer | 0.134 ± 0.0161 | 0.555 ± 0.0085 | 0.102 ± 0.0288 | 0.549 ± 0.0146 | 0.123 ± 0.0005 | 0.500 ± 0.0000 |
| | scGPT | 0.049 ± 0.0002 | 0.500 ± 0.0000 | 0.026 ± 0.0001 | 0.500 ± 0.0000 | 0.006 ± 0.0028 | 0.500 ± 0.0000 |
| | C2S (GPT-2 Large) | **0.149 ± 0.0057** | **0.564 ± 0.0030** | **0.202 ± 0.0059** | **0.600 ± 0.0029** | **0.152 ± 0.0062** | **0.574 ± 0.0032** |

| MODEL | T TEST (↑) | KS TEST (↑) | MMD (↓) | W (↓) |
|---|---|---|---|---|
| C2S (GPT-2 SMALL) | **2.96, $p = 0.003^*$** | **0.35, $p = 0.023^*$** | **$0.198 \pm 0.004$** | **$0.414 \pm 0.006$** |
| C2S (GPT-2 LARGE) | **2.85, $p = 0.004^*$** | **0.36, $p = 0.014^*$** | **$0.198 \pm 0.004$** | **$0.413 \pm 0.002$** |
| GPT-3.5-TURBO-1106 | 1.23, $p = 0.220$ | 0.21, $p = 0.392$ | $0.298 \pm 0.004$ | $0.490 \pm 0.008$ |
| MIXTRAL-8X7B-INSTRUCT AWQ | -1.20, $p = 0.233$ | 0.24, $p = 0.246$ | $0.639 \pm 0.016$ | $0.544 \pm 0.005$ |
| MISTRAL-7B-INSTRUCT | -8.64, $p = 0.384$ | 0.23, $p = 0.299$ | $0.754 \pm 0.010$ | $0.584 \pm 0.004$ |
| GPT-2 SMALL | 1.31, $p = 0.896$ | 1.52, $p = 0.783$ | $1.045 \pm 0.009$ | $0.752 \pm 0.004$ |
| GPT-2 LARGE | -1.44, $p = 0.885$ | 1.81, $p = 0.581$ | $0.939 \pm 0.006$ | $0.701 \pm 0.016$ |

FIG. 22

| Model | Accuracy (↑) | F1-score (↑) |
|---|---|---|
| C2S-Pythia-140M-1-cell | 38.18 | 0.3945 |
| C2S-Pythia-140M-3-cell | 40.36 | 0.4086 |
| C2S-Pythia-140M-5-cell | **41.64** | **0.4222** |
| C2S-Gemma-2B-1-cell | 54.30 | 0.5526 |
| C2S-Gemma-2B-5-cell | **73.70** | **0.7300** |

FIG. 23

ARTIFICIAL INTELLIGENCE SYSTEMS AND METHODS FOR ENABLING NATURAL LANGUAGE TRANSCRIPTOMICS ANALYSIS

CROSS-REFERENCE TO RELATED APPLICATIONS

This application claims priority to U.S. Provisional Patent Application Ser. No. 63/593,753, filed Oct. 27, 2023, which is hereby incorporated herein by reference in its entirety.

FEDERALLY SPONSORED RESEARCH STATEMENT

This invention was made with government support under Grant No. 1R35GM143072-01 awarded by the National Institutes of Health. The Government has certain rights in the invention.

FIELD

This technology generally relates to transcriptomics and, more particularly, to artificial intelligence methods and systems for enabling natural language transcriptomics analysis.

BACKGROUND

Large language models (LLMs), such as generative pre-trained transformers (GPTs), have demonstrated powerful capabilities in natural language processing (NLP) tasks including question answering, text classification, summarization, and text generation. However, applying LLMs to other domains like biology remains an open challenge. Alongside the development of LLMs for NLP, deep neural networks have been developed to accomplish numerous tasks on single cell transcriptomics data. Architectures have been described for several tasks including cellular annotation—where a cell is assigned a label according to its biological identity—, batch effect removal/sample integration—where transcript abundance differences due to technical replicates are removed—, and data imputation—where missing transcript abundance data are inferred.

More recently, efforts such as the Gene Expression Omnibus and Human Cell Atlas have centralized and standardized the storage of data from hundreds of single cell experiments across a wide range of tissues, comprising hundreds of millions of measurements. Several models have been designed and trained on this data (e.g., scGPT, scFoundation, and Geneformer), with the goal of creating a foundation model for single cell transcriptomics data analogous to foundation models in NLP. Additionally, publicly available datasets like Alpaca, and dataset generators such as Flan, together with parameter-efficient fine-tuning, have made it possible to train custom LLMs. However, current methods in the domain of single cell transcriptomic analysis unfortunately rely on specialized neural networks that do not leverage the pretrained knowledge and language understanding of LLMs, are inefficient, and are ineffective for facilitating natural language prompts and model outputs.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The disclosed technology is illustrated by way of example and not limitation in the accompanying figures, in which like references indicate similar elements:

FIG. 8 is a table illustrating the capacity of various LLMs generated according to the disclosed technology to generate valid genes and maintain an accurate sequence length;

FIG. 9 is a table illustrating the efficacy of models pretrained with natural language and then trained with cell sentences to generate meaningful text from cells through autoregressive prediction of cell types;

FIGS. 10A-10B illustrate perplexity curves for four models, including fine-tuned LLMs and LLMs trained only on cell sentences;

FIG. 11 is a table illustrating the ability of an LLM trained as described herein to generate realistic cells;

FIG. 13 is a table illustrating classification accuracy results against ground truth data for a KNN classifier fitted on ground truth cell sentences and used to predict the cell type label of generated cell sentences;

FIG. 14 is a table illustrating KNN classification results for separation of distinct cell types, which measures the ability of an exemplary LLM trained as described herein to generate distinct clusters when conditioned on cell type;

FIG. 15 is a table illustrating comparison results for cells generated via an exemplary LLM trained as described herein as and the real cells;

FIG. 16 is a table illustrating comparison results for cells generated via an exemplary LLM trained as described herein as and the real cells when using seen versus unseen prompts;

FIG. 17 is a table illustrating the performance of an exemplary LLM trained as described herein in predicting the effects of cytokine perturbations on immune cells;

FIG. 22 is a table illustrating the performance of an exemplary LLM trained as described herein via the mean cosine similarities between embeddings of generated abstracts and their respective original abstracts;

FIG. 23 is a table illustrating the performance of an exemplary LLM trained as described herein as a multi-cell context single-cell foundation model.

DETAILED DESCRIPTION

The technology described and illustrated herein extends the capabilities of large language models (LLMs) to the domain of transcriptomics by representing single-cell data in a text format amenable to causal language models. In particular, the transcriptomics system 102 of this technology transforms cell gene expression profiles into plaintext sequences of gene identifiers (e.g., gene names, gene symbols, or any other plaintext indicia of a particular gene) ordered by expression level. This rank transformation can advantageously be reverted with minimal loss of information and allows a pretrained causal language model to be further fine-tuned on cell sentences. Natural language pretraining followed by the training or fine-tuning described in detail below significantly improves LLM performance on transcriptomic tasks as compared to training only on annotated plaintext cell sequences, with performance additionally scaling with model size.

The fine-tuned LLMs disclosed herein can generate cells by completing sequences of gene identifiers, generate cells from natural language text prompts, and generate natural language text about cells. By leveraging LLMs' pretrained knowledge and combining both natural language and transcriptomics modalities, this technology enables LLMs that not only generate and interpret transcriptomics data, but also interact in natural language. By way of example only, applications of this technology include inferring how gene expression would change under perturbations, generating rare cell types, identifying gene markers, and interpreting transcriptomics via natural language. The capabilities of the disclosed technology aid biologists and advance single-cell research. Thus, applying the fine-tuned LLMs of this technology to single-cell transcriptomics enables new ways of analyzing, interpreting, and generating single-cell ribonucleic acid (RNA) sequencing data.

Figure 1:
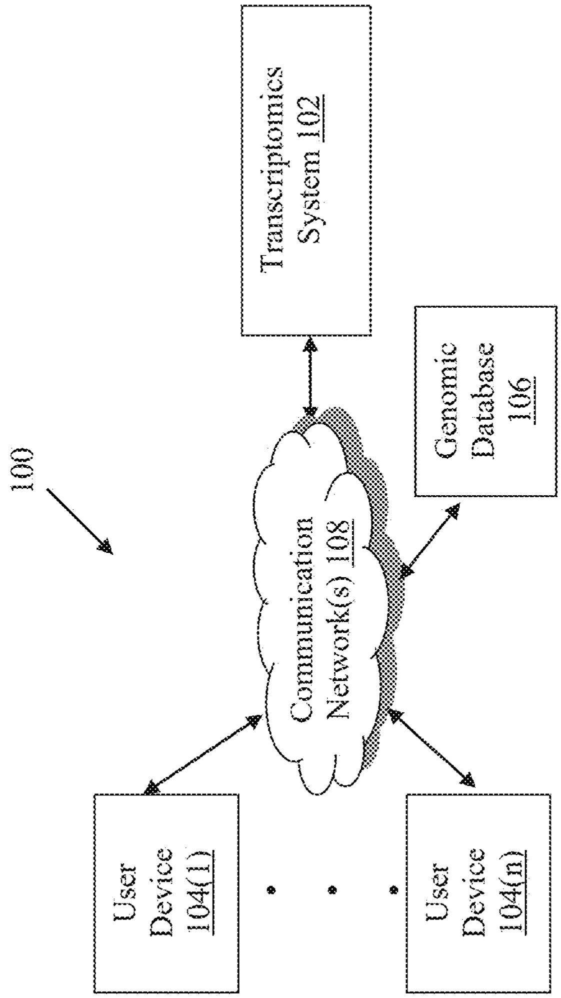
FIG. 1 is a block diagram of an exemplary network environment that includes a transcriptomics system.

Referring to FIG. 1, an exemplary network environment 100 that incorporates an exemplary transcriptomics system 102 is illustrated. The transcriptomics system 102 is coupled to user devices 104(1)-104(*n*) and a genomic database 106 via communication network(s) 108, although the transcriptomics system 102, user devices 104(1)-104(*n*), and genomic database 106 may be coupled together via other topologies. The network environment 100 also may include other network devices such as one or more routers or switches, for example, which are known in the art and thus will not be described herein. In this particular example, the transcriptomics system 102, user devices 104(1)-104(*n*), and genomic database 106 are disclosed in FIG. 1 as dedicated hardware devices. However, one or more of the transcriptomics system 102, user devices 104 (1)-104(*n*), or genomic database 106 can also be implemented in software within one or more other devices in the network environment 100.

Figure 2:
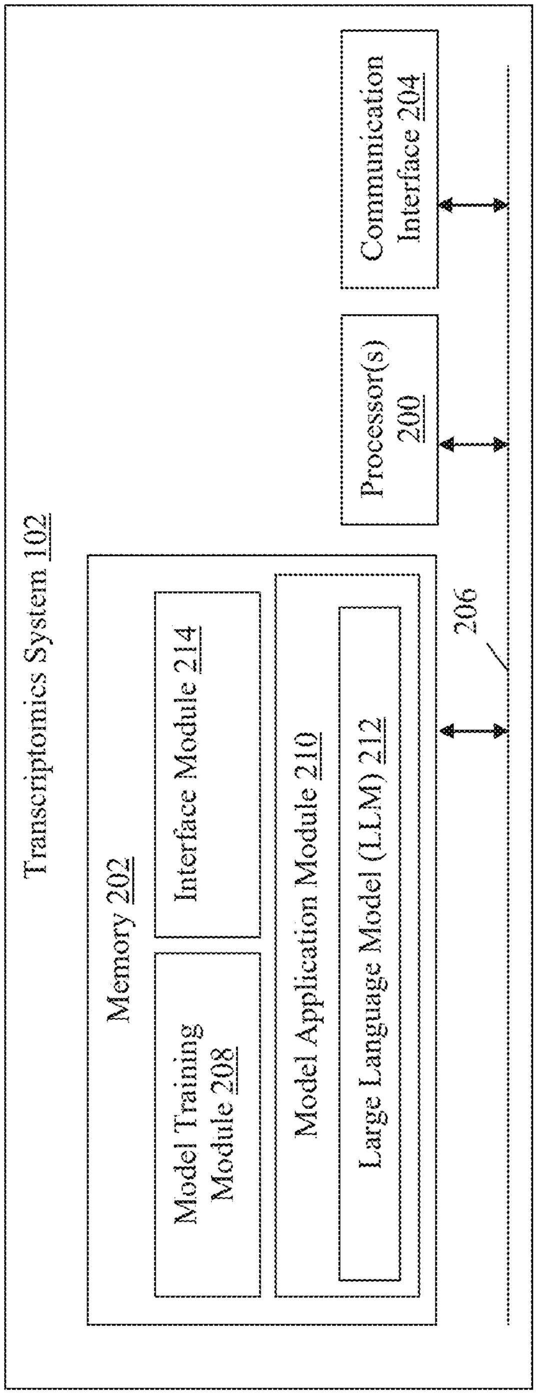
FIG. 2 is a block diagram of an exemplary transcriptomics system.

Referring to FIGS. 1-2, the transcriptomics system 102 may perform any number of functions, including training machine learning models, applying the trained machine learning models to enable natural language transcriptomics analysis based on prompts received via network messages from the user devices 104(1)-104(*n*), and providing graphical outputs and other displays to the user devices 104(1)-104(*n*) that include results of the application of the machine learning models, for example. The transcriptomics system 102 in this example includes processor(s) 200, memory 202, and a communication interface 204, which are coupled together by a bus 206, although the transcriptomics system 102 can include other types or numbers of elements in other configurations.

The processor(s) 200 of the transcriptomics system 102 may execute programmed instructions stored in the memory 202 of the transcriptomics system 102 for any number of the functions described and illustrated herein. The processor(s) 200 of the transcriptomics system 102 may include one or more central processing units (CPUs), one or more graphics processing units (GPUs), and/or processor(s) with one or more processing cores, for example, although other types of processor(s) can also be used.

The memory 202 of the transcriptomics system stores these programmed instructions for one or more aspects of the present technology as described and illustrated herein, although some or all of the programmed instructions could be stored elsewhere. A variety of different types of memory storage devices, such as random-access memory (RAM), read-only memory (ROM), hard disk, solid state drives, flash memory, or other computer readable medium that is read from and written to by a magnetic, optical, or other reading and writing system that is coupled to the processor (s) 200, can be used for the memory 202.

Accordingly, the memory 202 of the transcriptomics system 102 can store one or more modules that can include computer executable instructions that, when executed by the transcriptomics system 102, cause the transcriptomics system 102 to perform actions, such as to transmit, receive, or otherwise process messages and train and execute machine learning models, for example, and to perform other actions described and illustrated below with reference to FIGS. 3-9. The modules can be implemented as components of other modules and/or as applications, operating system extensions, plugins, or the like.

Even further, the modules may be operative in a cloud-based computing environment and/or executed within or as virtual machine(s) or virtual server(s) that may be managed in a cloud-based computing environment. Also, the modules, and even the transcriptomics system 102 itself, may be located in virtual server(s) running in a cloud-based computing environment rather than being tied to one or more specific physical network computing devices. Additionally, in one or more examples of this technology, virtual machine(s) running on the transcriptomics system 102 may be managed or supervised by a hypervisor.

In this particular example, the memory 202 of the transcriptomics system 102 includes a model training module 208, a model application module 210 with an LLM 212, and an interface module 214, although other types and/or number of modules can also be included in the memory in other examples. The model training module 208 in some examples is configured to pretrain an LLM using a natural language training data set and/or obtain an LLM pretrained for natural language processing (NLP) tasks. The model training module 208 is further configured to fine-tune the pretrained LLM based on genomic data for cells obtained from the genomic database 106 and transformed and annotated as described and illustrated in detail below. The fine-tuned LLM 212 can then be stored in the memory as part of the model application module 210, for example.

The interface module 214 in some examples is configured to provide a graphical interface to the user devices 104(1)-104(*n*) to facilitate input of natural language prompts, examples of which are discussed below. With the prompts, the interface module 214 can communicate with the model application module 210 to apply the LLM 212 and obtain a result. The interface module 214 is then configured to update the graphical interface, or provide a new graphical interface, to a requesting one of the user devices 104(1)-104(*n*) that includes the result.

Thus, the model application module 210 is configured to apply the LLM 212 to received prompts to generate results. The model application module 210 can be further configured to preprocess the prompts (e.g., for formatting) and/or post-process the results generated by the LLM 212. Exemplary post-processing methods are described and illustrated in detail below with reference to step 510 of FIG. 5.

Referring back to FIGS. 1-2, the communication interface 204 of the transcriptomics system 102 operatively couples and communicates between the transcriptomics system 102, user devices 104(1)-104(*n*), and genomic database 106, which are coupled together at least in part by the communication network(s) 108, although other types or numbers of communication networks or systems with other types or numbers of connections or configurations to other devices or elements can also be used. By way of example only, the communication network(s) 108 can include local area network(s) (LAN(s)) and/or wide area network(s) (WAN(s)) and can use TCP/IP over Ethernet, although other types or numbers of protocols can be used. The communication network(s) 108 in this example can employ any interface mechanisms and network communication technologies including, for example, Ethernet-based Packet Data Networks (PDNs).

While the transcriptomics system 102 is illustrated in this example as including a single device, the transcriptomics system 102 in other examples can include a plurality of devices each having one or more processors that implement one or more steps of this technology. In these examples, one or more of the devices can have a dedicated communication interface or memory. Alternatively, one or more of the devices can utilize the memory, communication interface, or other hardware or software components of one or more other devices included in the transcriptomics system 102. Additionally, one or more of the devices that together comprise the transcriptomics system 102 in other examples can be standalone devices or integrated with one or more other devices, such as one or more servers, for example. Moreover, one or more of the devices of the transcriptomics system 102 in these examples can be in a same or a different communication network including one or more public, private, or cloud networks, for example.

Each of the user devices 104(1)-104(*n*) of the network environment 100 in this example includes any type of computing device that can exchange network data, such as mobile, desktop, laptop, or tablet computing devices, virtual machines (including cloud-based computers), or the like. Each of the user devices 104(1)-104(*n*) in this example includes a processor, a memory, and a communication interface, which are coupled together by a bus or other communication link (not illustrated), although other numbers or types of components could also be used.

The user devices 104(1)-104(*n*) may run interface applications, such as standard web browsers or standalone client applications, which may provide an interface to make requests to, and received results from, the transcriptomics systems 102 via the communication network(s) 108. The user devices 104(1)-104(*n*) may further include a display device, such as a display screen or touchscreen, and/or an input device, such as a keyboard for example (not illustrated).

The genomic database 106 can store genomic data, such as a human tissue dataset from which a corpus of plaintext sequences of gene identifiers ordered by expression level (also referred to herein as cell sentences) for cells, which can be sampled to facilitate training of the LLM 212. The genomic database 106 can be a relational database (e.g., a Structured Query Language (SQL) database), although other types of databases can also be used in other examples.

Although the exemplary network environment 100 with the transcriptomics system 102, user devices 104(1)-104(*n*), genomic database 106, and communication network(s) 108 are described and illustrated herein, other types or numbers of systems, devices, components, or elements in other topologies can be used. It is to be understood that the systems of the examples described herein are for exemplary purposes, as many variations of the specific hardware and software used to implement the examples are possible, as will be appreciated by those skilled in the relevant art(s).

One or more of the components depicted in the network environment 100, such as the transcriptomics system 102, user devices 104(1)-104(*n*), or genomic database 106, for example, may be configured to operate as virtual instances on the same physical machine. In other words, one or more of the transcriptomics system 102, user devices 104(1)-104(*n*), or genomic database 106 may operate on the same physical device rather than as separate devices communicating through communication network(s) 108. Additionally, there may be more or fewer transcriptomics systems, user devices, or genomic databases than illustrated in FIG. 1.

In addition, two or more computing systems or devices can be substituted for any one of the systems or devices in any example. Accordingly, principles and advantages of distributed processing, such as redundancy and replication also can be implemented, as desired, to increase the robustness and performance of the devices and systems of the examples. The examples may also be implemented on computer system(s) that extend across any suitable network using any suitable interface mechanisms and traffic technologies, including by way of example only, wireless traffic networks, cellular traffic networks, Packet Data Networks (PDNs), the Internet, intranets, and combinations thereof.

The examples may also be embodied as one or more non-transitory computer readable media having instructions stored thereon, such as in the memory 202 of the transcriptomics system 102, for one or more aspects of the present technology, as described and illustrated by way of the examples herein. The instructions in some examples include executable code that, when executed by one or more processors, such as the processor(s) 200 of the transcriptomics system 102, cause the one or more processors to carry out steps necessary to implement the methods of the examples of this technology that are described and illustrated herein.

Figure 3:
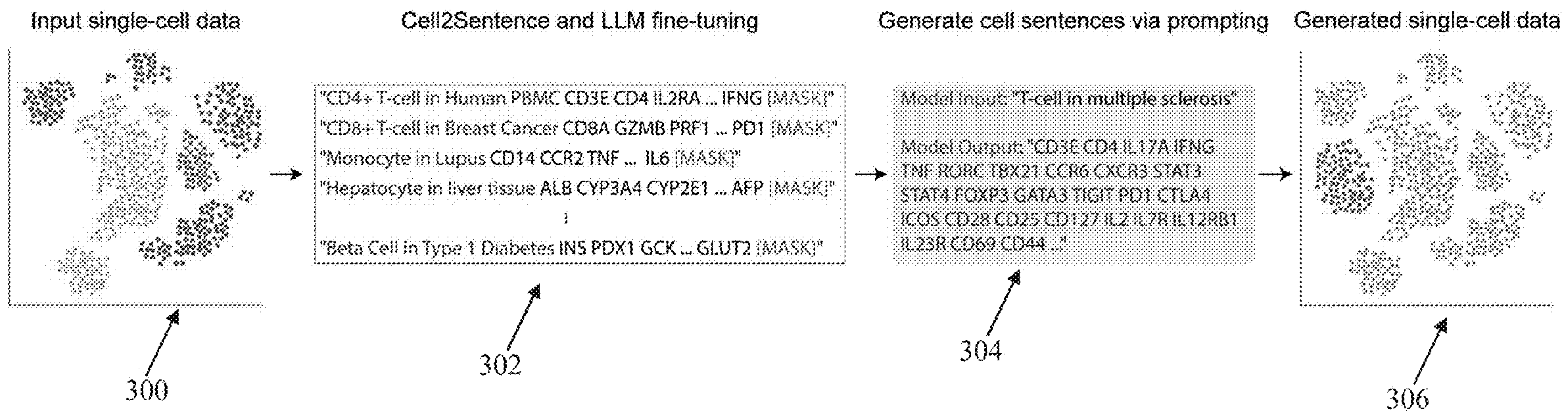
FIG. 3 is a flow diagram of an exemplary method to adapt large language models (LLMs) to a biological context.

Referring now to FIG. 3, a flow diagram of an exemplary method to adapt LLMs to a biological context, specifically single-cell transcriptomics in this particular example, is disclosed. In step 300, single-cell data is input, such as to the transcriptomics system 102 and from the genomics database 106, for example. The single-cell data includes gene expression data (e.g., a cell expression matrix or vector) that includes a relative expression level for each of a plurality of genes with respect to each of a plurality of cells. Optionally, the input single-cell data includes biological metadata, such as cell type, tissue, or disease, for example, although other types of metadata can also be used for conditioning in other examples.

In step 302, the transcriptomics system 102 represents the single-cell gene expression data as plaintext sequences by converting each of the cells' gene expression profile into a sequence of gene identifiers ordered by expression level and optionally annotated (e.g., prepended or appended) with corresponding biological or other metadata. The plaintext sequences, optionally annotated, are now referred to herein as "cell sentences" and are subsequently used by the transcriptomics system 102 in step 302 to fine-tune a causal language model (e.g., GPT-2 available from OpenAI Inc. of San Francisco, California). Optionally, the causal language model or LLM is pretrained for natural language tasks, which provides performance advantages explained in more detail below.

In step 304, the transcriptomics system 102 performs inferencing via prompting (e.g., prompts received from the user devices) to generate new cell sentences. The prompts can advantageously be received and processed by the fine-tuned LLM in a natural language format to generate a result (e.g., a new cell sentence, a cell type label, or a cell classification prediction), which is also in a plaintext format.

In step 306, the transcriptomics system 102 converts the plaintext sequences or cell sentences generated in step 304 back to gene expression space, as described and illustrated in more detail below. Advantageously, the application of the fine-tuned LLM 212 of this technology can generate biologically valid cells when prompted with a cell type and can also accurately predict cell type labels when prompted with cell sentences. Thus, the LLM 212 of this technology, which is fine-tuned using plaintext sequences of gene identifiers ordered by expression level for cells, can gain a biological understanding of single-cell data, while advantageously retaining their ability to generate text.

Figure 4A:
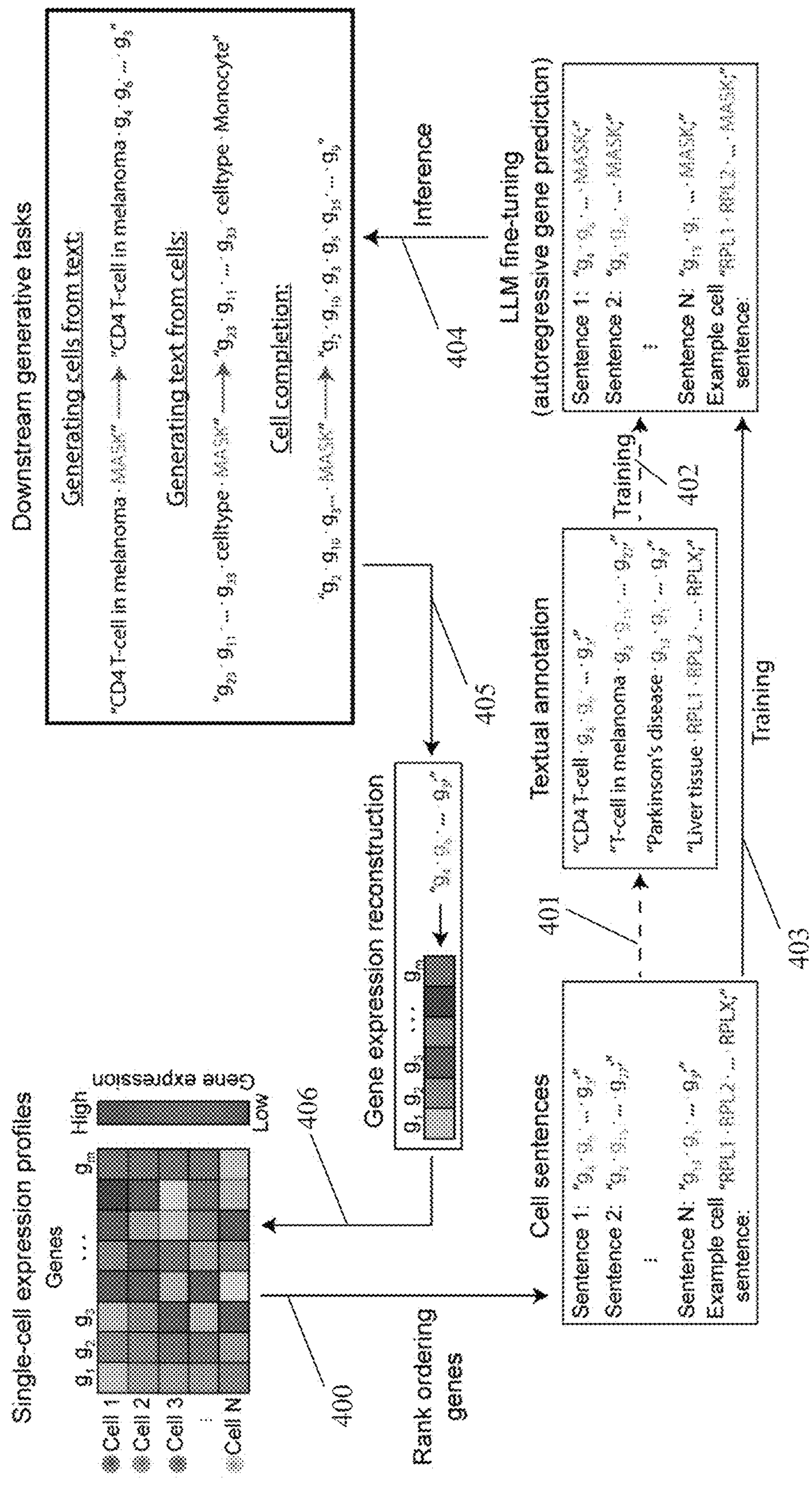
FIGS. 4A-4B illustrate flow diagrams of another exemplary method for adapting LLMs to a biological context.

Referring to FIG. 4A, a flow diagram of another exemplary method for adapting LLMs to a biological context is disclosed. In step 400 in this example, the transcriptomics system 102 generates cell sentences for cells in a plaintext format based on a rank ordering of gene identifiers according to gene expression levels indicated in single-cell gene expression profiles for the cells. Thus, this technology advantageously transforms data (i.e., gene expression profiles for cells) directly into a single format (i.e., text) prior to embedding.

In step 401, the transcriptomics system 102 optionally annotates the generated cell sentences with biological metadata, such as cell type, tissue, or disease. In the example illustrated in FIG. 4, respective ones of the cell sentences are annotated with "CD4 T-cell" cell type, "liver tissue" cell tissue, and "Parkinson's disease" disease, although any other type of biological or other metadata can also be used in other examples. Also optionally, the annotation can include prompt(s) (e.g., prepended or appended) to further mold or condition the LLM 212 training and fine-tuning.

In steps 402 and 403, the transcriptomics system 102 fine-tunes the LLM 212 via training using the annotated cell sentences generated in step 401 or the cell sentences generated in step 400, respectively. In some examples, the fine-tuned LLM 212 is pretrained to perform NLP tasks, as explained in more detail below. In some examples described and illustrated herein, the LLM 212 is trained using a human immune tissue dataset from which gene expression profiles are extracted and used to generate cell sentences subsequently used to fine-tune the LLM 212, but any other type of single-cell or other dataset can also be used in other examples.

An exemplary implementation of step 402 is described and illustrated in more detail below with reference to step 506 of FIG. 5. In some exemplary implementations of step 403, the transcriptomics system can use a GPT-2 small model initialized with 12 layers and 768 hidden dimensions or a GPT-2 medium model initialized with 24 layers and 1024 hidden dimensions. The transcriptomics system 102 can employ a learning rate of $6\times10-4$ with a cosine scheduler and 1% warmup ratio. For the GPT-2 medium model, gradients can be accumulated over 16 steps. The effective batch sizes for the small and medium GPT-2 models can be 10 and 48 examples, respectively.

Further, the transcriptomics system 102 can train a Byte Pair Encoding (BPE) tokenizer on a full cell sentence dataset, including natural language prompts and cell type labels, yielding a vocabulary of 9,609 tokens. The training set in some examples contains approximately 30 million tokens, averaging 740 tokens per example, although other types of training sets with different numbers of tokens can also be used. Due to the smaller embedding space, the initialized models contain slightly fewer parameters than their counterparts pretrained on a vocabulary of 50,257 tokens. The resulting corpus exhibits sparse natural language tokens due to short and repetitive prompts. A loss can be computed on both the prompt and the associated label (e.g., cell type). Not doing so could cause embeddings of the prompt tokens to remain random, impairing the capacity of the LLM 212 to learn the conditional relations between prompt and label tokens. The quality of the generated outputs in these examples is explained in more detail below with reference to FIG. 8.

In step 404, the transcriptomics system 102 performs inferencing, such as in response to prompts received from the user devices 104(1)-104(*n*). In some examples, inferencing is performed by generating cells via autoregressive cell completion, generating cells from text, or generating text from cells, although other types of results or model outputs can also be generated in other examples. Thus, the inferencing can generate plaintext cell sentences as downstream generative tasks in response to natural language prompts.

In steps 405-406, the transcriptomics system 102 reconstructs a gene expression profile (e.g., matrix or vector) of gene identifiers in the cell sentence generated in step 404 ordered according to expression level. Accordingly, the resulting generated cell sentences are converted back to gene expression corresponding to a biologically valid cell, for example. The gene expression level rank order transformation of step 400 can be reverted with minimal loss of information, as explained in more detail below with reference to FIGS. 7A-C, for example.

Figure 4B:
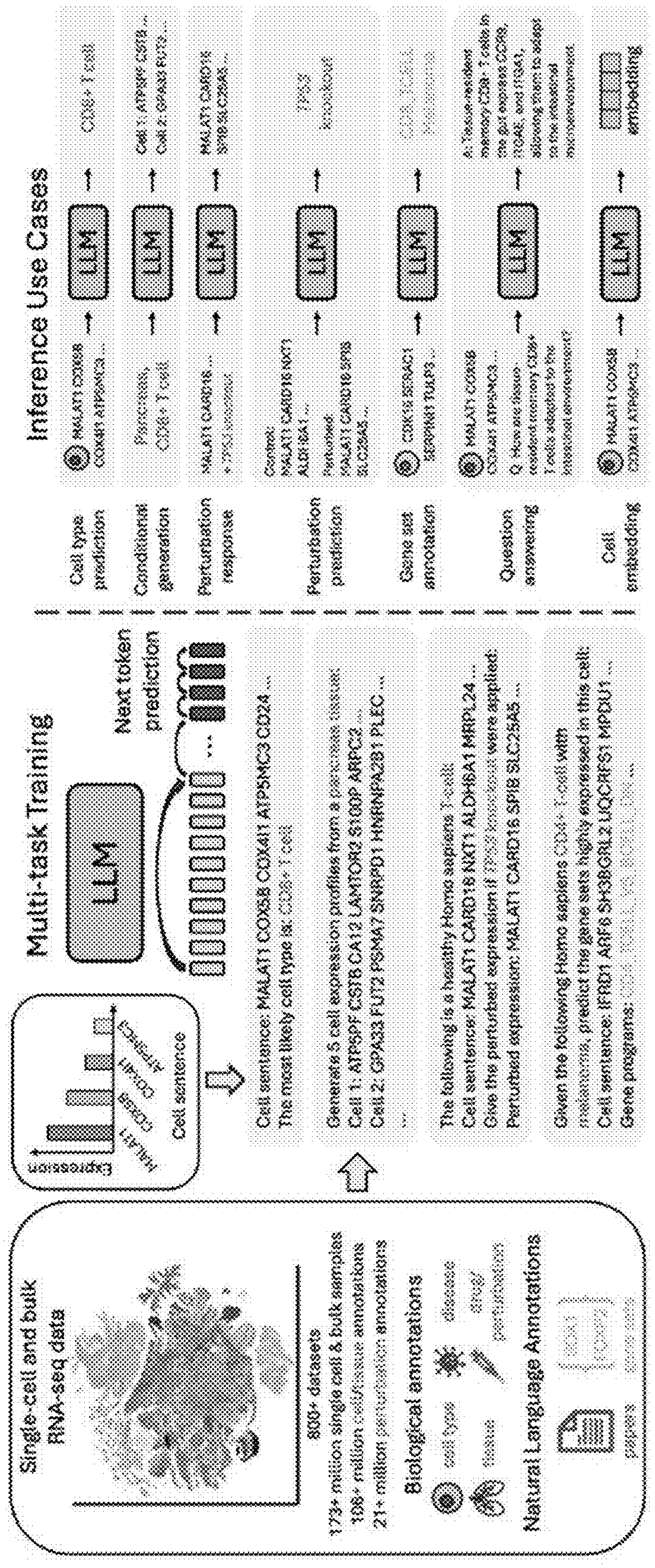

Referring to FIG. 4B, another flow diagram of another exemplary method for adapting LLMs to a biological context is disclosed. In this example, single-cell and bulk RNA-seq data from over 800 datasets (comprising 173+ million samples) were annotated with biological (e.g., cell type, species, tissue, and drug/perturbation) and natural language annotations (e.g., gene sets and scientific literature). During multi-task pretraining, the LLM 212 is fine-tuned using next-token prediction, where gene expression data are transformed into "cell sentences." In an inference phase, various biological tasks, including cell type prediction, conditional generation, perturbation response prediction, gene set annotation, question-answering, and cell embedding generation, are supported illustrating the versatility of this technology for single-cell data analysis and interpretation.

Figure 5:
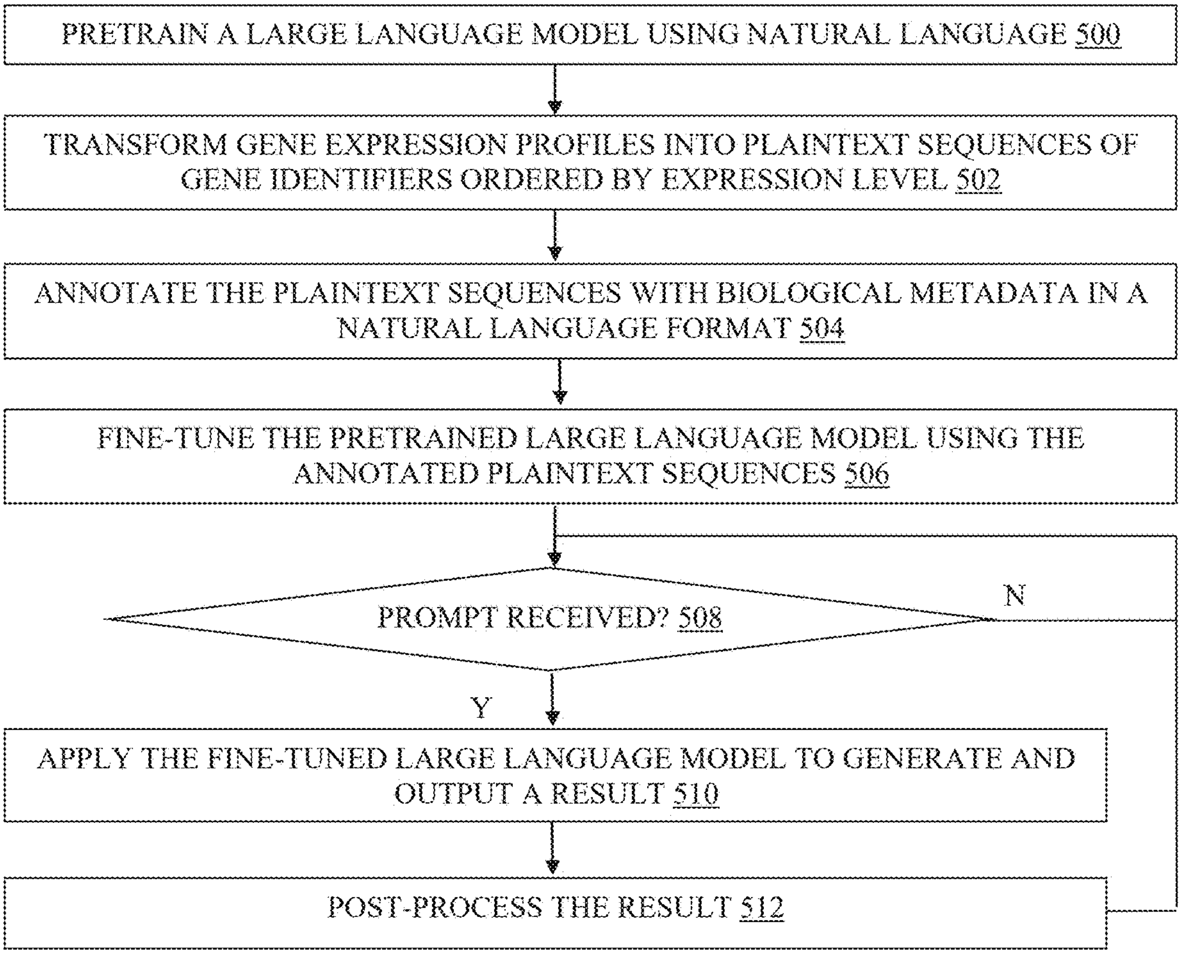
FIG. 5 is a flowchart of an exemplary method for enabling natural language transcriptomics analysis.

Referring more specifically to FIG. 5, a flowchart of an exemplary method for enabling natural language transcriptomics analysis is illustrated. In step 500 in this example, the transcriptomics system 102 pretrains an LLM 212 using natural language and such that the LLM 212 can perform NLP tasks above an accuracy threshold. In other examples, the transcriptomics system 102 obtains a pretrained LLM that is subsequently fine-tuned as explained in more detail below. For example, a pretrained LLM using third-party libraries such as Hugging Face Transformers disclosed in Thomas Wolf et al. "HuggingFace's Transformers: State-of-the-art Natural Language Processing." 2020. arXiv: 1910.03771 [cs.CL], which is incorporated by reference herein in its entirety, can be used to streamline LLM 212 deployment.

In step 502, the transcriptomics system 102 transforms gene expression profiles into plaintext sequences or cell sentences of gene identifiers ordered by expression level. The transformation in step 502 is a reorganization of the cell expression matrix into sequences of gene identifiers ordered by decreasing transcript abundance. The transformation in step 502 advantageously creates a robust and reversible encoding of the biological data.

For example, let C denote a cell by gene count matrix with n rows and k genes, with Ci,j denoting the number of RNA molecules observed for gene j in cell i. Optionally, standard preprocessing steps for single-cell RNA sequence data, including filtering cells with fewer than 200 genes expressed and filtering genes which are expressed in fewer than 200 cells, can be followed. Quality control metrics are then calculated based on mitochondrial gene counts within each cell (e.g., using the Scanpy Python library disclosed in F Alexander Wolf, Philipp Angerer, and Fabian J Theis. "SCANPY: large-scale single-cell gene expression data analysis". In: Genome biology 19 (2018), pp. 1-5, which is incorporated by reference herein in its entirety), and low-quality cells are filtered out which contain over 2500 counts, or which have greater than 20 percent of transcript counts from mitochondrial genes.

The count matrix is then row-normalized so that each cell sums up to 10,000 transcript counts and then log-normalized (e.g., as disclosed in Ashraful Haque et al. "A practical guide to single-cell RNA-sequencing for biomedical research and clinical applications". In: Genome medicine 9.1 (2017), pp. 1-12., which is incorporated by reference herein in its entirety), to obtain a final preprocessed count matrix C'. This normalization step can be summarized as:

$$C'_{i,j} = \log_{10}\left(1 + 10^4 \times \frac{C_{i,j}}{\sum_{j=1}^{k} C_{i,k}}\right)$$

The rank-order transformation applied on C' is denoted as S, and the sequence of gene identifiers resulting from S(Ci) is denoted as cell sentence si for each cell i in the preprocessed count matrix. While gene identifiers are ordered based on expression level in some of the examples disclosed herein, gene identifiers can also be ordered by any matric computed from the count matrix data (e.g., variability or relative expression as defined by z-score, quantile norm, or other techniques) in other examples. Optionally, the preprocessing and rank-order transformation S can be applied on each individual single-cell dataset, providing a flexible process for converting traditional single-cell gene expression count matrices to cell sentences.

A dataset can then be generated by sampling 49,920 cells from a large dataset of human immune tissue cells that can be obtained as described in C Dominguez Conde et al. "Cross-tissue immune cell analysis reveals tissue-specific features in humans," In: Science 376.6594 (2022), eab15197, which is incorporated by reference herein in its entirety, for example, although the dataset can be obtained from other sources and genomic data for other types of tissue cells can also be used. The normalization steps described above can be applied and the results converted to cell sentences, optionally split into training (39,936), validation (4,992), and test (4,992) sets. To limit computational costs, each cell sentence can be truncated to only keep gene identifiers for the 100 highest expressed (i.e., top 100 ranked) genes. This optional truncation operation minimizes the resulting ordering variability, as genes with lower rank have more similar expression values.

In step 504, the transcriptomics system 102 optionally annotates the plaintext sequences generated in step 502 with biological metadata in a natural language format. For example, in the large dataset of human immune tissue cells disclosed above, each cell's type can be prepended to the corresponding cell sentence. Cell sentences can be integrated with textual annotation in step 504 to perform both generation and summarization tasks, both of which benefit from natural language pretraining optionally performed in step 500. The annotations optionally include prompts in addition to or in place of biological metadata, which can be prepended to cell sentences, for example.

In some examples, the annotation in step 504 can be based on Gene Set Enrichment Analysis (GSEA) data (e.g., Gene Ontology (GO) and/or Kyoto Encyclopedia of Genes and Genomes (KEGG) data), which can be integrated to annotate cell sentences with textual gene set labels or descriptions for cells that are enriched for these gene sets. In other examples, the annotation is based on publication (e.g., manuscript or abstract) text for cell sentences that come from the data associated with the publication, gene knowledge base data (e.g., annotation label with a list of associated genes), and/or metadata labels (e.g., species, cell type, tissue, experimental condition, perturbation, disease, or measurement technology).

In yet other examples, the gene identifiers can be modified to include additional metadata as the annotation. For example, instead of creating cell sentences with textual gene symbols, the transcriptomics system 102 can create custom gene-to-text mapping with functional groups, promoter/enhancer region features, etc. Other types of biological metadata or other textual data can also be used and combined with genomic data in other exemplary iterations of step 504.

In step 506, the transcriptomics system 102 fine-tunes the LLM 323 pretrained in step 500 using the plaintext sequences annotated in step 504. During the fine-tuning, for each iteration, a task is randomly selected, and a corresponding prompt template is subsequently picked from a set of templates per task. These templates, while optionally varied in phrasing, retain consistent semantic meaning in this example.

In step 508, the transcriptomics system 102 determines whether a prompt has been received, such as from one of the user devices 104(1)-104(*n*). Advantageously, the technology described and illustrated herein allows for interaction with genomic data via natural language.

Figure 6:
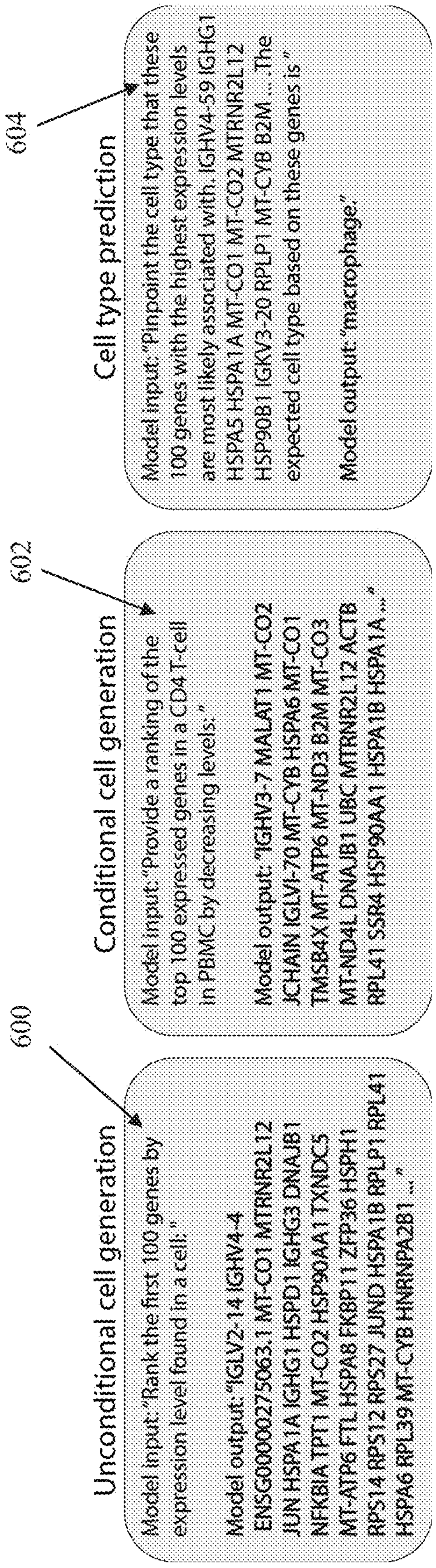
FIG. 6 illustrates three exemplary types of prompts used during LLM fine-tuning and result generation including unconditional cell generation, conditional cell generation, and autoregressive cell type prediction.

Referring to FIG. 6, three exemplary types of prompts used during fine-tuning in step 506 and generation in step 510 are illustrated including unconditional cell generation prompt 600, conditional cell generation prompt 602 (e.g., with cell type), and autoregressive cell type prediction prompt 604. The prompt structure for cell type prediction combines the prompt with the cell sentence and is used to generate a cell type label following a provided sequence of genes. For the conditional cell generation prompt 602, the structure merges the prompt with the specified cell type, which is used to generate a sequence of genes given a specific cell type label. In contrast, the unconditional cell generation prompt 600 primarily consists of a succinct directive, which can be used to produce a sequence of genes without any prescribed cell type label. Other types of prompts can be received in step 508 and/or used in training and/or generation steps in other examples.

If the transcriptomics system 102 determines in step 508 that a prompt has not been received from one of the user devices 104(1)-104(*n*), then the No branch is taken back to step 508 and the transcriptomics system effectively waits for a prompt to be received. However, if a prompt is received from one of the user devices 104(1)-104(*n*), then the Yes branch is taken to step 510.

In step 510, the transcriptomics system 102 applies the fine-tuned LLM 212 to generate and output a result, which in some examples is a cell sentence. Potential applications of this technology include inferring how gene expression would change under perturbations, generating rare cell types, identifying gene markers, and interpreting transcriptomics via natural language. Such capabilities could aid biologists and advance single-cell research. For example, a prompt received in step 508, and subsequent application of the fine-tuned LLM 212 in step 510, can facilitate simulation of the effect of perturbagen(s) on a provided cell (e.g., when there are non-additive or synergistic effects of co-treatment), interpretation of biology of a provided cell or set of cells via natural language, or generation a set of cells based on a natural language description prompt.

In other examples, a prompt received in step 508, and subsequent application of the fine-tuned LLM 212 in step 510, can facilitate a translation of a cell from one species to another (e.g., a mouse cell defined as a prompt can yield a human cell of the same type/function/context), cross-species translation inclusive of all cross-genetic basis translations (e.g., from one immortalized cell line to another or from immortalized cell line to human tissue prediction in vivo), and/or a translation of a cell from one context to another (e.g., how a T-cell in the blood changes when it enters the brain, skin, or liver). In yet other examples, additional context is provided by multiple cells so that a prompt received in step 508 can be used to predict cell type and tissue labels with improved performance facilitated by the integration of data from multiple cells to reveal richer biological relationships. Many other applications and capabilities could aid biologists and advance single-cell research in other examples. In some examples, the output or result is generated until an end-of-sequence (EOS) token is predicted or encountered, which was appended to training samples used in step 506.

In step 512 in this example, the transcriptomics system 102 post-processes the result output by the application of the fine-tuned LLM 212 in step 510. The natural language output from the LLM 212 fine-tuned using cell sentences is unusable directly in some examples without specific post-processing (e.g., to ensure that generated gene identifiers are meaningful and that genes are not duplicated in a cell sentence). In some examples, gene and cell type extraction is done using regex to remove prompts.

Gene rank and gene expression follow a log-linear relationship in scRNAseq data. Single-cell RNA sequencing produces transcript count matrices that represent the genetic profiles of individual cells. Most current computational models in single-cell biology concentrate on handling data in R×n, posing scalability challenges with larger datasets. The technology described and illustrated herein transforms expression matrices into gene sequences to enable the use of LLMs and other transformer-based architectures for single-cell data analysis.

While genes are not intrinsically ordered in transcript matrices, their expression patterns have been shown to follow inverse-rank frequency patterns, thus establishing a steady relationship between a gene's expression level within a cell and its rank among the genes expressed in that cell. This inverse-rank relationship can be modeled with a log-linear distribution and approximated in log-log space using a linear regression. The resulting models allow conversion of cells between gene rank and expression domains. This capability is leveraged to produce rank-ordered sequences of gene identifiers that can be used to fine-tune the LLM 212 in step 506.

Thus, this technology enables forward and reverse transformation with minimal information loss. For evaluation, invalid genes are retained and ranks of duplicate genes are averaged, resulting in rearrangement of sequences as needed. When reverting to expression values, invalid genes are ignored, but the rank values are preserved (e.g., if an invalid gene appears in position 3 and a valid gene appears in position 4, the invalid gene is ignored, but the valid gene retains a rank of 4).

In examples in which the result is a cell sentence, the post-processing of step 512 transforms the generated cell sentence back to gene expression space (e.g., gene expression vectors) via an inverse transformation function. More specifically, to transform generated cell sentences back to expression space, the transcriptomics system 102 uses a linear model to predict the expression of the generated gene based on its rank. For a given single-cell dataset that underwent rank-order transformation S, let ridenote the log of the rank of gene i in C, and $e_i$ the original expression of gene i. The transcriptomics system 102 first fits a linear model to predict $e_i$ from $r_i$ during the initial conversion to cell sentence format, resulting in a fitted slope and intercept value, which are saved for each converted dataset. Hence, a linear regression of the form $e_i=a_d \times r_i+b_i$, given dataset d and $\{a_d,b_d\} \in R^2$ can be fit.

The fitted linear model parameters are then applied to the log of the rank of the generated genes to convert the sequence of genes back to an expression vector. Any genes that are not present in the generated cell sentence are considered to have zero expression and are filled with zeros in the resulting expression vector. The transcriptomics system 102 defines the average rank of a generated gene $$g_i^{gen}$$

belonging to the out of unique genes $G_U \subseteq S$ as follows:

$$r_i^{gen} = \frac{1}{|G|}\sum_{j=1}^{|G|} \text{rank}(g_j^{gen}),$$

where $$G = \{g_1^{gen}, g_2^{gen}, \ldots , g_n^{gen}\} \subseteq S$$

is the set of duplicate generated genes for $$g_i^{gen}\text{, and } r_i^{gen}$$

and $_{gen}$ denotes the average rank of gene $g_i$ in the generated cell sentence, which yields the following formulation for expression value vector for the generated cell:

$$e_i^{gen} = \begin{cases} a_d \times \log(r_i^{gen}) + b_d & \text{if } g_i^{gen} \in G \\ 0 & \text{otherwise} \end{cases}.$$

Subsequent to post-processing the result in step 512, the transcriptomics system 102 proceeds back to step 508 and wait to receive another prompt from the same or another one of the user devices in this example.

Figure 7B:
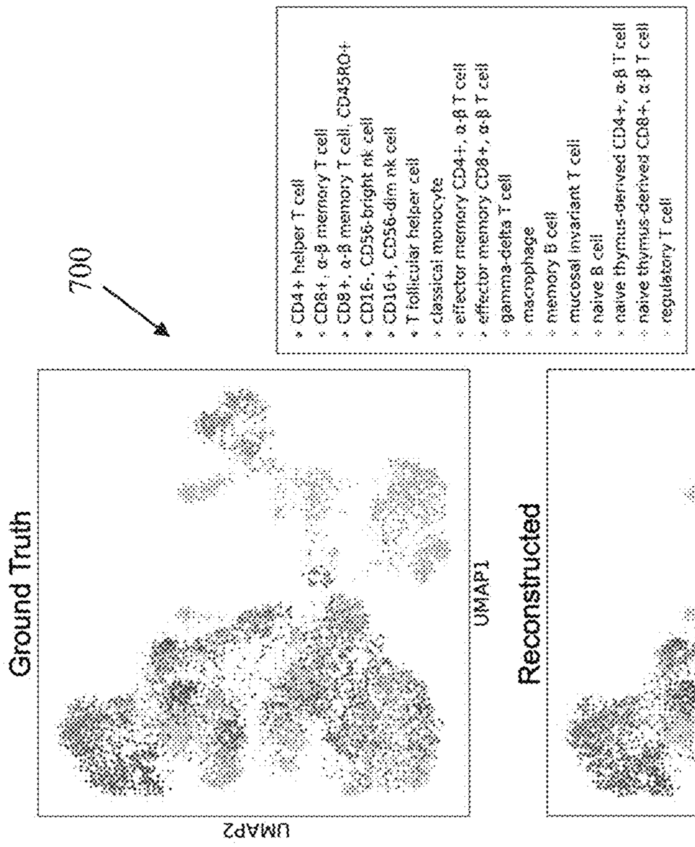
FIGS. 7A-7C illustrate graphs illustrating the accuracy of cell expression reconstruction from cell sentences.
Figure 7A:
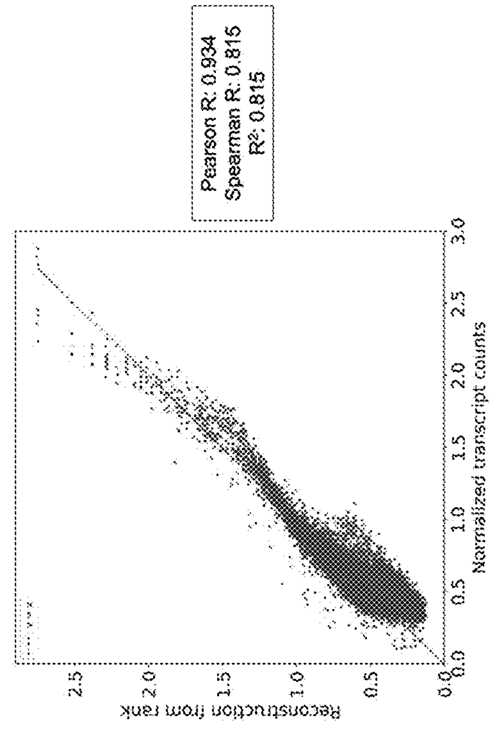
Figure 7C:
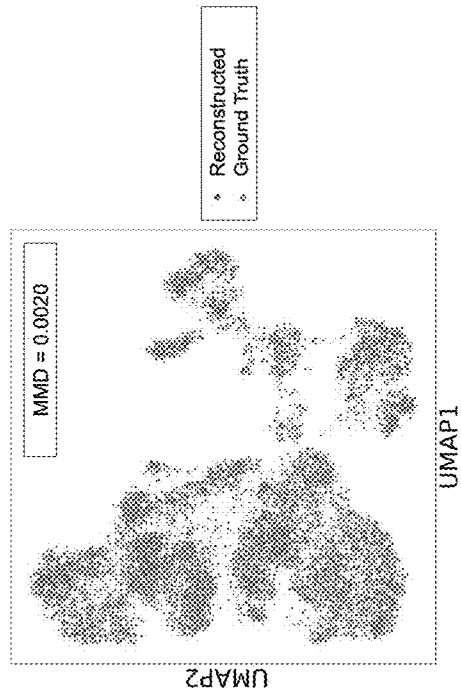

Referring to FIGS. 7A-C, graphs illustrating the accuracy of cell expression reconstruction from cell sentences, as may be performed in the post-processing of step 512, are illustrated. Referring more specifically to FIG. 7A, the reconstruction performance of a fitted linear regression on an immune tissue dataset comprising 50K cells and over 35K genes is illustrated. A linear model captures over 81% of the variation in the gene expression, requiring only the log rank value of that gene for expression reconstruction. This demonstrates that the transformation to cell sentences and back to expression space preserves much of the important information in single-cell data, which allows for analysis in the natural language space of cell sentences followed by accurate conversion back to expression.

FIGS. 7B-C visualize the original ground truth immune tissue data alongside reconstructed expression data from converted cell sentences. Specifically, in FIG. 7B, the uniform manifold approximation and projection (UMAP) plot of ground truth expression 700 versus reconstructed expression from cell sentences 702 is illustrated. FIG. 7C illustrates the UMAP plot of ground truth expression and reconstructed expression from cell sentences overlaid. FIGS. 7B-C qualitatively show that important structure in the immune tissue data as well as cell type separation are retained.

Accordingly, as described and illustrated by way of the examples herein, the cell sentences of this technology conveniently and correctly encode gene expression data in a format easily digestible by an LLM 212. The LLM 212 fine-tuned on these cell sentences not only converge robustly, but also performs significantly better on tasks related to cell sentences as compared to models trained from scratch or other current deep learning models purpose-built for handling single-cell RNA sequencing data.

In the disclosed examples, both the LLMs trained only on cell sentences (also referred to herein as C2S) (e.g., as disclosed with reference to step 403) as well as the LLMs generated by fine-tuning a pretrained LLM in step 506 (also referred to herein as NL+C2S) have been evaluated. Both types of LLMs can use an AdamW optimizer (e.g., as disclosed in Ilya Loshchilov and Frank Hutter. "Decoupled weight decay regularization". In: arXiv preprint arXiv: 1711.05101 (2017), which is incorporated herein by reference in its entirety), half precision floating points (FP16) and gradient accumulation for memory savings, and the same cell sentence corpus. Negligible improvement can be gained using full-precision floating points (FP32) at the cost of a 60% slowdown.

Additionally, both types of LLMs can be initialized using pretrained weights from the Hugging Face model hub at HF Canonical Model Maintainers. gpt2 (Revision 909a290). 2022. DOI: 10.57967/hf/0039. URL: https://huggingface.co/gpt2, which is incorporated by reference herein in its entirety. A learning rate of $5\times10^{-5}$ can be employed with a linear scheduler, gradients can be accumulated over 16 steps, and batch sizes of eight examples can be used (yielding an effective gradient update batch size of 128 examples). For the fine-tuned LLM 212, the loss was computed exclusively on labels. Additionally, the pretrained GPT-2 tokenizer, which averages around 233 tokens per training samples (yielding a total of 9M training tokens), was used.

The capacity of various LLMs generated according to the disclosed technology to generate valid genes and maintain an accurate sequence length (e.g., 100 genes) is illustrated in FIG. 8. The metrics in FIG. 8 were computed across 35 cell types seen during training with 500 cells generated per cell type and then averaged across all generated cells (for the top 100 genes). The valid genes percentage shows the number of genes generated that are real genes including duplicates. The generated length is the number of genes generated regardless of their validity. The unique gene ratio is the ratio of unique valid genes to the generated length. Accordingly, both GPT-2 small and medium LLMs trained only on cell sentences can generate sequences of 100 genes without significantly deviating from the mean. Those LLMs also both achieve over 97% and 96% accuracy in gene validity and uniqueness. LLMs trained using cell sentences can generate real genes with few duplicates and nonsense genes.

However, LLMs pretrained with natural language generate more accurately. The fine-tuned LLM 212 outperform the LLMs trained only on cell sentences by generating genes with over 99% validity and 98% uniqueness on average. While both types of LLMs achieve reliable performance by these standard metrics, the fine-tuned LLM 212 consistently outperforms the LLMs trained only on cell sentences in generating real human genes, which are only rarely duplicated within cell sentences.

Accordingly, models pretrained with natural language can be trained with cell sentences to generate meaningful text from cells. The results in FIG. 9 illustrate the efficacy of this approach through autoregressive prediction of cell types. The exemplary approaches disclosed herein are distinct from traditional classification—a classifier head is not trained nor is any architecture modified, and instead the LLM 212 is prompted with a cell sentence and asked to identify its cell type in natural language. The results in FIG. 9 show that accuracy significantly improves with natural language pre-training. The scores are computed on unseen immune tissue test data and weighted by the distribution of labels. As illustrated above, a significant performance decline is observed when using LLMs that have not undergone natural language pretraining, thereby confirming that the LLM 212 is not merely memorizing the conditioning text. Furthermore, a modest performance increment is observed as the scale of pretrained LLMs increases.

Further, LLMs trained on cell sentences show healthy convergence behavior. Infusing sequential structure to single-cell data yields a non-trivial and meaningful textual modality. Four GPT-2 models were trained on a corpus of cell sentences as explained above. Referring to FIGS. 10A-10B, perplexity curves for four models, including fine-tuned LLMs and LLMs trained only on cell sentences, are illustrated. Specifically, FIG. 10A illustrates an estimated model perplexity computed after the training loss. FIG. 8B illustrates an estimated model perplexity computed on the validation set during training. All models preserve the default GPT-2 context length of 1024 tokens.

As illustrated in FIGS. 10A-10B, the models generated according to the disclosed technology learn cell sentence distributions and converge during training with a steadily decreasing perplexity. Additionally, larger models achieve lower perplexities. Overall, the causal language models of this technology are capable of learning cell sentence semantic distribution from a narrow scRNA-seq dataset.

Accurate generation of different cell types is crucial for generative approaches on single-cell data, as it enables downstream analysis. To evaluate the ability of the LLM 212 trained as described herein to generate realistic cells, the average generated cell of 17 cell types in an immune tissue dataset was considered and is compared in FIG. 11 with the average real cell of each cell type. Across 17 different cell types, generated cells from the fine-tuned LLM 212 show high correlation with real cells, capturing over 94% of the variation in the expression of an average cell. Initializing the LLM 212 with a pretrained language model outperforms training from scratch, indicating that there is mutual information which allows the LLM 212 to better understand cell sentence generation.

Even further, the LLM 212 generated according to the examples described and illustrated herein can meaningfully manipulate cells as text. The k-Nearest Neighbors (KNN) accuracy for generated cells was calculated using two distinct methods: (1) Classify the generated cell type based on the types of its nearest neighbors in the ground-truth dataset and (2) Classify the generated cell type based on the types of its generated neighbors. The label assigned to a generated cell corresponds to the cell type used for its conditional generation. Predictions of type 1 determine if the LLM is capable of approximating real cells within the corresponding cell type, whereas predictions of type 2 show the LLM 212 can generate distinct cell types.

Referring to FIGS. 12A-12F, UMAP plots for cell sentences and expression data are illustrated. The UMAP plots show how much separation can be achieved by representing cells with the 100 highest expressed genes. Unlike reducing the size of the gene expression matrix by selecting a subset of highly variable genes, the disclosed approach allows different cells to be encoded with the specific genes that are most relevant to them, potentially allowing for better representation of rare cell types at similar levels of compression. Additionally, since the immune dataset has many sub-types for some cell types (e.g., T-cells), some sub-types will be very close when restricted to the 100 genes with the highest expression. Still, non-trivial structure emerges in all of the UMAP plots illustrated in FIGS. 12A-12F.

Figures 12A, 12B, 12C, 12D, 12E, 12F:
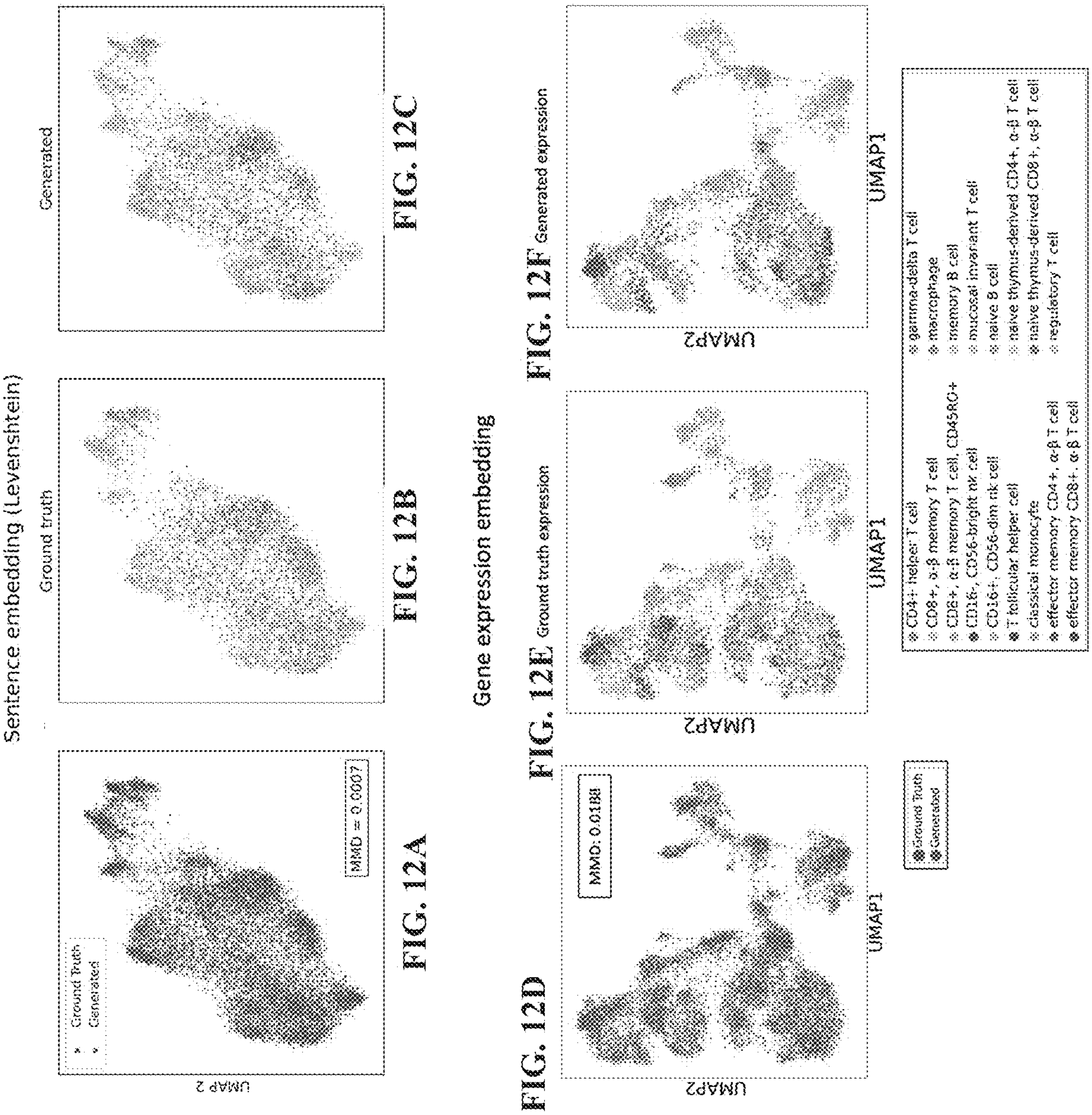
FIGS. 12A-12F illustrate uniform manifold approximation and projection (UMAP) plots for cell sentences and expression data.

Thus, the UMAP plots of FIGS. 12A-12F show that the LLM 212 pretrained with natural language and fine-tuned with cell sentences achieves quality generated outputs in the sentence space. Good cell type separation is illustrated for both generated and ground truth cell sentences in addition to good overlap, showing that the generated sentences model the ground truth distribution well. The UMAP plots in FIGS. 12A-12C are of generated cell sentences versus real cell sentences using Levenshtein distance. The Maximum Mean Discrepancy (MMD) statistic was computed with the Python library scMMD.

The UMAP plots in FIGS. 12D-12F are of generated cell expression vectors and ground truth cell expression vectors. In FIGS. 12C-12D, the UMAP plots demonstrate that the reconstructed gene expression from the top 100 generated genes not only maintains the general structure of the original data but also closely aligns with cell type-specific distinctions in the baseline UMAP visualizations. This validates the ability of the generative LLM 212 to capture both macroscopic and fine-grained expression profiles, attesting to its efficacy in creating biologically relevant cellular representations.

Quantification of the UMAP plots of FIGS. 12A-12F is provided in FIGS. 13-14. Specifically, FIG. 13 provides the KNN classification accuracy results against ground truth data. A KNN classifier was fitted on ground truth cell sentences and used to predict the cell type label of generated cell sentences from different trained models. KNN classification was done both in cell sentence space using Levenshtein distance (Lev.), as well as after converting back to expression vectors (Expr.). "Real cells" indicates KNN classification fit on ground truth cell sentences and used to predict a separate sample of ground truth cell sentences.

Additionally, FIG. 14 provides KNN classification results for separation of distinct cell types, which measures the ability of the LLM 212 to generate distinct clusters when conditioned on cell type. This analysis is also done both in cell sentence space using Levenshtein distance (Lev.), as well as after converting back into expression vectors (Expr.).

Accordingly, with this technology, the fine-tuned LLM 212 can generate cells by completing sequences of gene identifiers, generate cells from natural language text prompts, and generate natural language text about cells. By leveraging the pretrained natural language knowledge of the LLM 212 and combining both modalities, this technology enables the LLM 212 to not only generate and interpret transcriptomics data, but also advantageously interact in natural language.

Several exemplary testing results will now be described with reference to practical applications of this technology. In a conditional cell generation example, 500 cells were sampled with replacement from each cell type in a held out immune dataset for comparison. The k-nearest neighbors (k-NN) classifier was fit on the held out immune cells with their cell types used as labels. The true label of a generated cell was the cell type used for its conditional generation. Gromov-Wasserstein (GW) distance was measured between all generated and all held out cells. The full cell generation LLM 212 (also referred to herein as "C2S" or "Cell2Sentence") outperformed all models across different values of k (3, 5, 10, 25). The accuracy values for the LLM 212 (e.g., 0.2588±0.0061 for k=3) indicate that cells generated via the LLM 212 are closer to the real cells when compared using k-NN classification, as illustrated in FIG. 15.

Additionally, the GW distance for the LLM 212 (54.3040=0.3410) was significantly lower compared to other models, showing a superior ability to generate cells that resemble the true distribution. This distance indicates that the LLM 212 maintains high fidelity to the original data, making it the most effective model for preserving biological characteristics.

The k-NN performance when using seen versus unseen prompts was also compared for cell type generation with the same setup as in the above example except that the unseen prompts were new prompts generated by GPT-4, which were not used during training. The results demonstrate some robustness to variability in prompts, as reflected in FIG. 16.

In another example, the performance of the LLM 212 was evaluated in predicting the effects of cytokine perturbations on immune cells, compared to scGEN and scGPT. The LLM 212 achieved significantly higher correlations across Pearson R and Spearman R metrics. For instance, the LLM 212 achieved a Pearson R of 0.9241±0.0002, compared to scGEN's 0.6805±0.0075 and scGPT's 0.0041±0.0018, as reflected in FIG. 17. This performance demonstrates the superior capability of the LLM 212 in generating unseen perturbations effectively, further highlighting its robustness and potential impact.

In this example, a dataset comprising combinatorial cytokine stimulation of immune cells was used. The Pearson R and Spearman R values were computed using the mean expression vectors in the unseen test dataset and the corresponding mean expression vectors generated by the LLM 212. The top 5000 highly variable genes were selected based on the training dataset, and the top 20 most differentially expressed genes between exposures of the same cell type and perturbation were computed from those 5000 highly variable genes. The A symbol indicates the correlations based on differencing with the mean expression vector of the opposite exposure in the training dataset. The conditioning labels are combinatorial, consisting of triples of cell type, cytokine stimulation, and exposure. There are 140 possible combinations in total, and the models were tasked with generating 10 cell type/perturbation combinations with different exposures from those seen during training. The LLM 212 showed superior performance in generating unseen exposures of perturbations compared to SOTA perturbation methods scGEN and scGPT.

Figure 18:
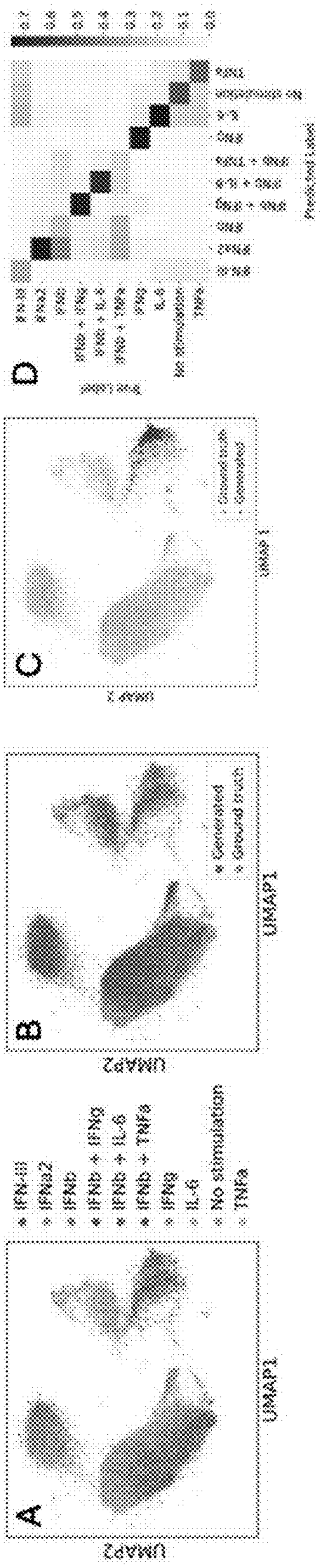
FIG. 18 illustrates exemplary testing results of an exemplary transcriptomics system to simulate responses to combinatorial cytokine stimulation.
Figure 19:
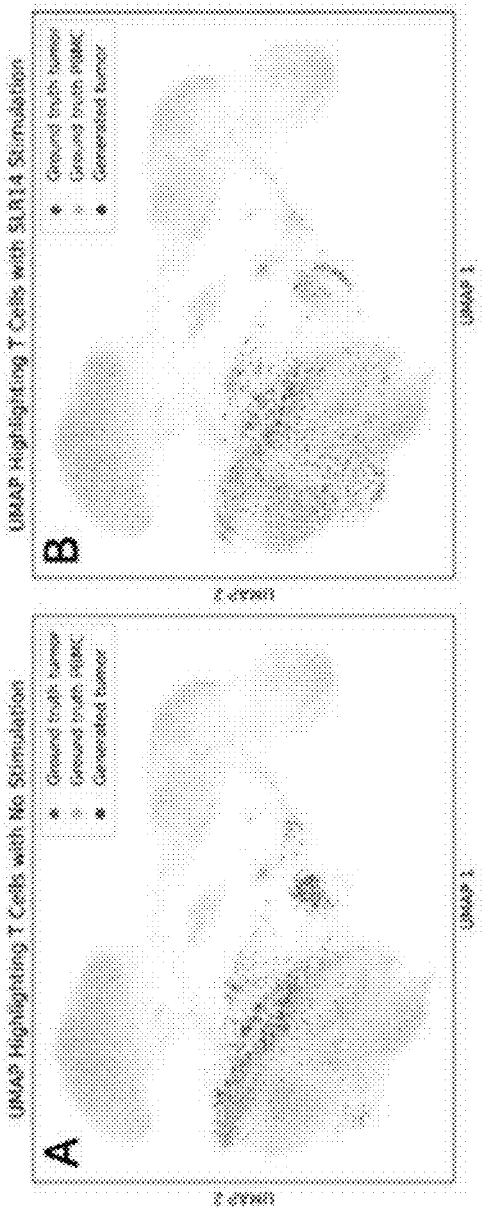
FIG. 19 illustrates exemplary testing results of an exemplary transcriptomics system to predict tumor immune responses in PERCEPT data.

In another example, the LLM 212 was applied to PERCEPT experiments involving cytokine-stimulated PBMCs, predicting the effects of previously unseen perturbations, including interferons on monocytes and the combined effect of IFNb and IL-6, as shown in FIG. 18. Using the LLM 212 on melanoma tumor samples, the immunostimulatory effects of therapies like aPD-1 in T cells were predicted. We show that Stimulations producing an anti-viral or dsRNA sensing response, using reagents like the novel RIG-I agonist SLR14, enhance anti-tumor immunity with distinct effects in tumor-derived immune cells compared with PBMCs, as illustrated in FIG. 19. Notably, the LLM 212 outperformed other approaches for predicting perturbation responses.

Figures 20, 21:
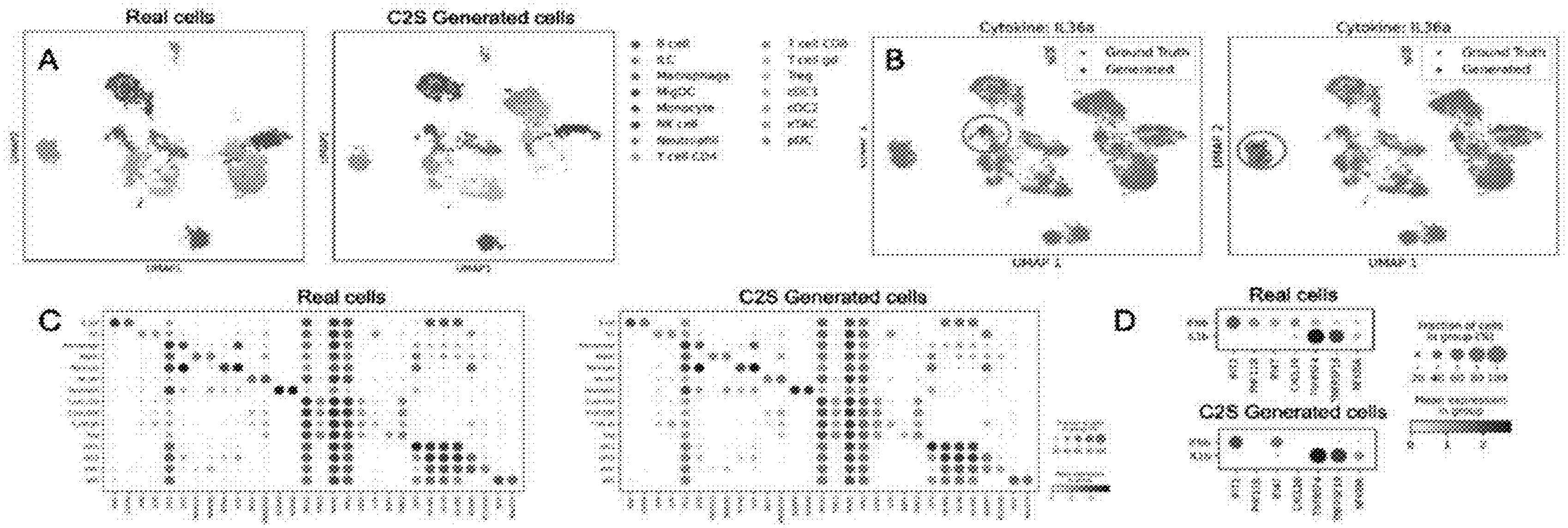
FIG. 20 illustrates exemplary testing results of an exemplary transcriptomics system that simulates cytokine responses in mouse lymph nodes.
FIG. 21 is a table illustrating the performance of an exemplary LLM trained as described herein for downstream classification of cell label.

Additionally, the LLM 212 was trained on a dataset of single-cell transcriptomic profiles of 15 immune cell types in response to 86 cytokines, covering over 1,400 cytokine-cell type combinations in mouse lymph nodes in vivo. Responses to cytokine stimulation in held-out data were accurately simulated, demonstrating the effectiveness in simulating in vivo cellular responses of the LLM 212. FIG. 20 shows that generated cells closely match ground truth, highlighting the ability of the LLM 212 to capture complex gene expression patterns effectively.

In a cell label prediction example, the performance of the LLM 212 was evaluated for downstream classification of cell labels, which include multiple metadata components (e.g., cell type, perturbation, or dosage). The LLM 212 achieved significantly higher accuracy and AUROC compared to other methods across all conditions tested (i.e., cytokine stimulation, L1000, and GTEx). For instance, under partial label conditions for cytokine stimulation, the LLM 212 model achieved an accuracy of 0.639±0.0049 and an AUROC of 0.767±0.0049, outperforming models like XGBoost, Geneformer, and scGPT, as illustrated in FIG. 21, which demonstrates that the LLM 212 provides superior predictive accuracy and reliability, even when classifying complex combinatorial metadata.

In the example associated with the results in FIG. 21, cell labels were composed of multiple combinatorial metadata parts, including cell type, perturbations, and dosage information. Accuracy and area under ROC curve was computed on model predictions versus ground truth combinatorial labels, with partial credit given for partial misclassifications.

In a natural language interpretation example, statistical analyses, including T-tests and KS tests, were used to evaluate the performance of the LLM 212 via the mean cosine similarities between embeddings of generated abstracts and their respective original abstracts. The LLM 212 achieved a T-test value of 2.85 (p=0.004) and a KS test value of 0.36 (p=0.014), as reflected in FIG. 22, indicating a statistically significant improvement over other methods, such as GPT-3.5-Turbo-1106 and Mistral-7B (MMD). Additionally, the LLM 212 demonstrated lower Maximum Mean Discrepancy and Wasserstein (W) distance values, suggesting a closer alignment of embeddings from summaries generated via the LLM 212 to those of the original abstracts and outperforming all baseline approaches.

In another natural language interpretation example, the LLM 212 was used to predict biological annotations, such as gene set enrichment analysis (GSEA) and gene program associations. The LLM 212 accurately predicted gene programs associated with cells, demonstrates that the LLM 212 can effectively interpret raw gene expression data and convert it into meaningful biological annotations, which can be translated into natural language descriptions. This capability of the disclosed technology illustrates the versatility of the LLM 212 in bridging the gap between raw biological data and interpretable insights.

In yet another example, a multi-cell version of the LLM 212 was created, in accordance with the technology described herein, which handles up to five cells in one context, although any number of cells could be used in other examples. In this example, predicting cell type and tissue labels with the LLM 212 significantly outperformed single-cell context models, as illustrated in FIG. 23. In this particular example, the LLM 212 was trained on an immune tissue dataset and took multiple cell sentences, which, across two base architectures, demonstrated consistent improvement in tissue classification accuracy on immune tissue types when more cells are given as input.

This improvement, due to the additional context provided by multiple cells, demonstrates the effectiveness of the disclosed technology to successfully train multi-cell context foundation models. Additionally, the LLM 212 in this example can integrate data from multiple cells to reveal richer biological relationships. 3- and 5-cell versions of the LLM 212 outperform 1-cell models in various downstream tasks, showing that incorporating data from multiple cells within a tissue or condition enhances the ability of the LLM 212 to interpret complex biological interactions.

In other examples relating to multi-species, the LLM 212 was applied for cross-species analysis, focusing on embedding and translation between mouse and human cells. When the LLM 212 is trained on multi-species data (e.g., mouse and human), the LLM 212 embeddings can be used to embed both mouse and human cells in the same latent space. Specifically, cell sentences and their LLM 212 sentence embeddings can allow for a joint analysis of mouse and human cells, which enables comparisons and insights across species at the cellular level.

Furthermore, the LLM 212 can "translate" between species, using pairs of human and mouse cells during training and generating mouse cells from human (or vice versa) during inference. These cell pairs can be obtained by aligning cells from the same tissue or organ using optimal transport methods. This cross-species translation capability paves the way for comparative studies and functional transfer between species.

Figure 24A:
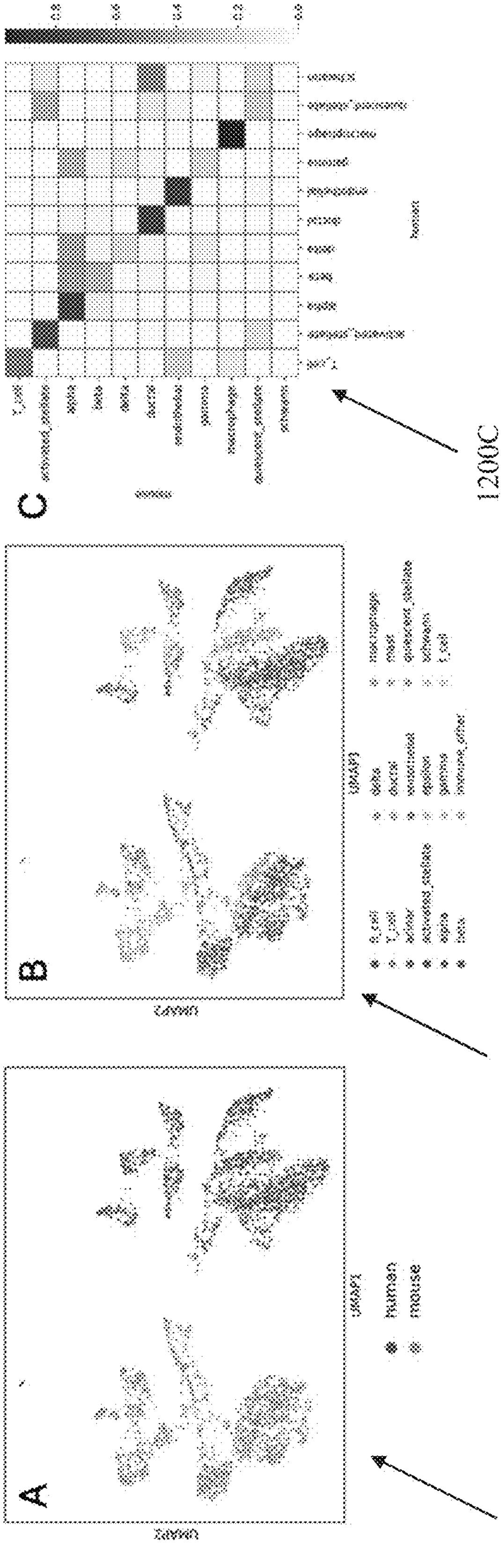
FIGS. 24A-B illustrate exemplary cross-species analysis testing results of an exemplary transcriptomics system.
Figure 24B:
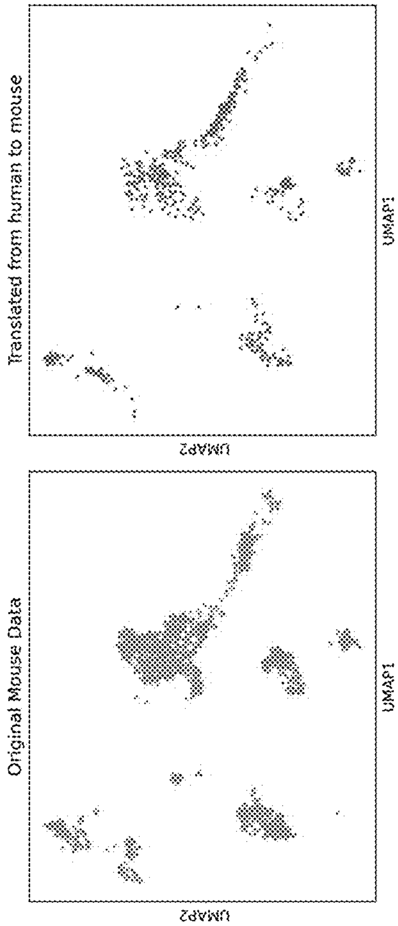

FIGS. 24A-24B illustrates how the LLM 212 can enable cross-species embedding, providing a multi-species embedding that allows for optimal transport mapping of cell types across species. Panels 1200A-B include UMAP embeddings of human and mouse pancreas data are shown, where both species are embedded in the same latent space using the LLM 212. Panel 1200C demonstrates the optimal transport mapping, highlighting the alignment of cell types between human and mouse. Additionally, FIG. 24B shows generative translation with the LLM 212 in which mouse cells were generated (human to mouse translated) from provided human cells. These results indicate that the LLM 212 can effectively embed multiple species into a shared latent space, allowing for joint analysis and comparison of cellular behaviors across species. This ability to map cell types across species has significant implications for cross-species functional studies and the transfer of biological insights from model organisms to human biology.

The results in these examples emphasize the advantages and practical applications of the disclosed technology in generating biologically accurate cell types, predicting complex perturbation responses, performing downstream classification tasks, generating high-quality abstract summaries, predicting cytokine responses, effectively modeling multi-cell contexts, predicting biological annotations, and cross-species embedding and translation. The superior accuracy, similarity metrics, and robustness reflect the ability of the LLM 212 to effectively bridge language modeling and single-cell transcriptomics, outperforming current techniques. The demonstrated robustness to unseen prompts, superior prediction of perturbation effects, enhanced downstream classification performance, quality of abstract generation, simulation of cytokine responses, success in modeling multi-cell contexts, effective annotation of biological data, and cross-species analysis further highlight the adaptability and scalability of this biomedical artificial intelligence technology.

Having thus described the basic concept of the invention, it will be rather apparent to those skilled in the art that the foregoing detailed disclosure is intended to be presented by way of example only and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations, therefore, is not intended to limit the claimed processes to any order except as may be specified in the claims. Accordingly, the invention is limited only by the following claims and equivalents thereto.

What is claimed is:

1. A method for enabling natural language transcriptomics analysis, the method implemented by one or more transcriptomics systems and comprising:

transforming genomic data including gene expression profiles for cells into sequences of genes ordered by expression level for each of the cells;

annotating the sequences of genes with metadata in a natural language format;

fine-tuning a large language model (LLM) using the annotated sequences of genes, wherein the LLM is pretrained for natural language processing (NLP) tasks; and applying the fine-tuned LLM to generate and output a result in response to a prompt received in the natural language format.

2. The method of claim 1, further comprising applying an inverse transformation function to the result to generate a gene expression vector for a single cell.

3. The method of claim 1, wherein the result comprises a cell sentence comprising a sequence of gene identifiers ordered by expression level, a cell type label, or a cell classification prediction.

4. The method of claim 1, wherein the metadata comprises one or more of a cell type, a tissue type, a disease, a species, an experimental condition, a perturbation, a measurement technology, a prompt, publication text, or gene knowledgebase data.

5. The method of claim 1, wherein the prompt corresponds to an unconditional cell generation used to generate a sequence of genes without a cell type label, a conditional cell generation used to generate another sequence of genes given another cell type label, or an autoregressive cell type prediction used to generate an additional cell type label proximate an additional sequence of genes.

6. The method of claim 1, wherein the sequences of genes comprise plaintext sequences of gene identifiers or gene symbols.

7. The method of claim 1, further comprising pretraining the LLM with textual data for the NLP tasks before fine-tuning the LLM.

8. A transcriptomics system, comprising memory with instructions stored thereon and one or more processors configured to execute the stored instructions to:

train a large language model (LLM) with textual data for natural language processing (NLP) tasks to generate a pretrained LLM;

transform genomic data including gene expression profiles for cells into sequences of genes ordered by expression level for each of the cells;

annotate the sequences of genes with metadata in a natural language format;

train the pretrained LLM using the annotated sequences of genes to generate a fine-tuned LLM;

receive a prompt in the natural language format from a user device via a graphical user interface provided to the user device;

apply the fine-tuned LLM to the prompt to generate a result; and provide the result to the user device via the graphical user interface in response to the prompt.

9. The transcriptomics system of claim 8, wherein the one or more processors are further configured to execute the stored instructions to apply an inverse transformation function to the result to generate a gene expression vector for a single cell.

10. The transcriptomics system of claim 8, wherein the result comprises a cell sentence comprising a sequence of gene identifiers ordered by expression level, a cell type label, or a cell classification prediction.

11. The transcriptomics system of claim 8, wherein the metadata comprises one or more of a cell type, a tissue type, a disease, a species, an experimental condition, a perturbation, a measurement technology, a prompt, publication text, or gene knowledgebase data.

12. The transcriptomics system of claim 8, wherein the prompt corresponds to an unconditional cell generation used to generate a sequence of genes without a cell type label, a conditional cell generation used to generate another sequence of genes given another cell type label, or an autoregressive cell type prediction used to generate an additional cell type label proximate an additional sequence of genes.

13. The transcriptomics system of claim 8, wherein the sequences of genes comprise plaintext sequences of gene identifiers or gene symbols.

14. A non-transitory computer readable medium having stored thereon instructions comprising executable code that, when executed by one or more processors, causes the one or more processors to:

train a large language model (LLM) with textual data for natural language processing (NLP) tasks to generate a pretrained LLM;

train the pretrained LLM using sequences of genes to generate a fine-tuned LLM, wherein the sequences of genes are annotated with metadata in a natural language format;

apply the fine-tuned LLM to a prompt in the natural language format received from a user device to generate a result; and provide the result to the user device in response to the prompt.

15. The non-transitory computer readable medium of claim 14, wherein the executable code, when executed by the one or more processors, further causes the one or more processors to transform genomic data including gene expression profiles for cells into the sequences of genes ordered by expression level for each of the cells.

16. The non-transitory computer readable medium of claim 14, wherein the executable code, when executed by the one or more processors, further causes the one or more processors to apply an inverse transformation function to the result to generate a gene expression vector for a single cell.

17. The non-transitory computer readable medium of claim 14, wherein the result comprises a cell sentence comprising a sequence of gene identifiers ordered by expression level, a cell type label, or a cell classification prediction.

18. The non-transitory computer readable medium of claim 14, wherein the metadata comprises one or more of a cell type, a tissue type, a disease, a species, an experimental condition, a perturbation, a measurement technology, a prompt, publication text, or gene knowledgebase data.

19. The non-transitory computer readable medium of claim 14, wherein the prompt corresponds to an unconditional cell generation used to generate a sequence of genes without a cell type label, a conditional cell generation used to generate another sequence of genes given another cell type label, or an autoregressive cell type prediction used to generate an additional cell type label proximate an additional sequence of genes.

20. The non-transitory computer readable medium of claim 14, wherein the sequences of genes comprise plaintext sequences of gene identifiers or gene symbols.

* * * * *